(12) United States Patent
Bradley et al.

(10) Patent No.: US 7,544,500 B2
(45) Date of Patent: Jun. 9, 2009

(54) PROCESS FOR THE PRODUCTION OF A REVERSIBLY INACTIVE ACIDIFIED PLASMIN COMPOSITION

(75) Inventors: Rita T. Bradley, Cary, NC (US); Scott A. Cook, Garner, NC (US); Christopher A. Dadd, Holly Springs, NC (US); Jonathan D. Kent, Holly Springs, NC (US); Marina N. Korneyeva, Raleigh, NC (US); Valery V. Novokhatny, Raleigh, NC (US); James F. Rebbeor, Garner, NC (US); Christopher J. Stenland, Cary, NC (US); Jonathan S. Strauss, Walnut Creek, NC (US); Jarrett C. Terry, Raleigh, NC (US); Jeffrey A. Yuziuk, Garner, NC (US)

(73) Assignee: Talecris Biotherapeutics, Inc., Research Triangle Park, NC (US)

( * ) Notice: Subject to any disclaimer, the term of this patent is extended or adjusted under 35 U.S.C. 154(b) by 637 days.

(21) Appl. No.: 10/692,105

(22) Filed: Oct. 23, 2003

(65) Prior Publication Data

US 2004/0171103 A1 Sep. 2, 2004

Related U.S. Application Data

(63) Continuation-in-part of application No. 10/143,156, filed on May 10, 2002, which is a continuation of application No. PCT/US00/42143, filed on Nov. 13, 2000, which is a continuation-in-part of application No. 09/438,331, filed on Nov. 13, 1999, now Pat. No. 6,355,243.

(51) Int. Cl.
*C12N 9/50* (2006.01)
*C12N 9/68* (2006.01)
*C12N 9/70* (2006.01)

(52) U.S. Cl. .................. 435/219; 435/217; 435/216

(58) Field of Classification Search .................. None
See application file for complete search history.

(56) References Cited

U.S. PATENT DOCUMENTS

| | | | |
|---|---|---|---|
| 3,434,929 A | 3/1969 | Buck et al. | |
| 3,950,513 A | 4/1976 | Jensen | |
| 4,082,612 A | 4/1978 | Robbins et al. | |
| 4,115,551 A | 9/1978 | Lormeau et al. | |
| 4,177,262 A | 12/1979 | Lormeau et al. | |
| 4,259,448 A | 3/1981 | Nakamura et al. | |
| 4,361,652 A | 11/1982 | Uemura et al. | |
| 4,361,653 A | 11/1982 | Watanabe et al. | |
| 4,442,213 A | 4/1984 | Heber et al. | |
| 4,446,316 A | 5/1984 | Chazov et al. | |
| 4,462,980 A | 7/1984 | Diedrichsen et al. | |
| 4,499,073 A | 2/1985 | Tenold | |
| 4,663,146 A | 5/1987 | Morser et al. | |
| 4,774,087 A | 9/1988 | Wu et al. | |
| 4,908,204 A | 3/1990 | Robinson et al. | |
| 5,024,829 A | 6/1991 | Berger et al. | |
| 5,096,637 A | 3/1992 | DiLeo et al. | |
| 5,165,912 A | 11/1992 | Selmer et al. | |
| 5,237,050 A | 8/1993 | Boyle et al. | |
| 5,288,489 A | 2/1994 | Reich et al. | |
| 5,290,692 A | 3/1994 | Suzuki et al. | |
| 5,304,383 A | 4/1994 | Eibl et al. | |
| 5,328,996 A | 7/1994 | Boyle | |
| 5,407,673 A | 4/1995 | Reich et al. | |
| 5,472,692 A | 12/1995 | Liu et al. | |
| 5,728,674 A | 3/1998 | Sprecher et al. | |
| 5,767,269 A | 6/1998 | Hirsh et al. | |
| 5,776,452 A | 7/1998 | Eibl et al. | |
| 5,879,923 A | 3/1999 | Yago et al. | |
| 6,139,819 A | 10/2000 | Unger et al. | |
| 6,207,066 B1 * | 3/2001 | Trese et al. | |
| 6,479,253 B1 | 11/2002 | Silver et al. | |

FOREIGN PATENT DOCUMENTS

| | | | |
|---|---|---|---|
| CN | 1 167 823 A | | 12/1997 |
| EP | 0256836 A1 | | 8/1987 |
| EP | 0 399 321 A2 | | 11/1990 |
| GB | 904478 | | 8/1962 |
| GB | 2 090 599 A | | 7/1982 |

(Continued)

OTHER PUBLICATIONS http://www.lakesidepress.com/pulmonary/books/physiology/chap7_1.htm, Chapter 7: Acid-Base Balance.*
Kline, D.L., "The Purification and Crystallization of Plasminogen (Profibrinolysin)," *Journal of Biological Chemistry*, 204: 949-955 (1953).

(Continued)

*Primary Examiner*—Michele Flood
(74) *Attorney, Agent, or Firm*—Womble Carlyle Sandridge & Rice PLLC

(57) ABSTRACT

Disclosed is both a process for producing a reversibly inactive acidified plasmin by activating plasminogen and a process for producing a purified plasminogen. The produced plasmin is isolated and stored with a low pH-buffering capacity agent to provide a substantially stable formulation. The purified plasminogen is typically purified from a fraction obtained in the separation of immunoglobulin from Fraction II+III chromatographic process and eluted at a low pH. The reversibly inactive acidified plasmin may be used in the administration of a thrombolytic therapy.

23 Claims, 12 Drawing Sheets

FOREIGN PATENT DOCUMENTS

| | | |
|---|---|---|
| JP | 0207 8633 | 3/1990 |
| JP | 09 065895 A | 3/1997 |
| RO | 103 682 A | 12/1991 |
| WO | WO 87/06836 A | 11/1987 |
| WO | WO 93/15189 A | 8/1993 |
| WO | WO 95 04077 A1 | 2/1995 |
| WO | WO 97/15572 | 5/1997 |
| WO | WO 98/37086 * | 8/1998 |

OTHER PUBLICATIONS

Supplementary Partial European Search Report (EP 00 99 1956, dated Dec. 17, 2004).
Binder, B.R., et al., "Purification and Characterization of Human Vascular Plasminogen Activator Derived from Blood Vessel Perfusates," *Journal of Biological Chemistry*, 254(6): 1998-2003 (1979).
Castellino, F.J., et al., "Rabbit Plasminogen and Plasmin Isozymes," *Methods in Enzymology*, 45: 273-286 (1976).
Robbins, K.C., et al., "Human Plasminogen and Plasmin," *Methods in Enzymology*, 19: 184-199 (1970).
International Search Report (PCT/US03/34020, dated Jul. 27, 2004).
European Supplementary Partial Search Report (EP 00 97 8572, dated Jul. 16, 2004).
European Supplementary Partial Search Report (EP 00 99 1956, dated Jun. 1, 2004).
European Supplementary Partial Search Report (EP 00 99 0910, dated May 25, 2004).
Ambrus, C., et al., "Insolubilized Activators of the Fibrinolysin System," *J. Med.* 3: 270-281 (1972).
Ambrus, J.L., et al., "Clinical Pharmacology of various types of fibrinolytic enzyme preparations," *Am. J. Cardiol.*, 6:462-475 (1960).
Amris, C.J., et al., "Effect of Plasmin Therapy on Blood Coagulation and on Plasma Proteins in Patients with Cancer," *Danish Medical Bulletin*, 11(5): 141-145 (1964).
Amris, C.J., et al., "Turnover and Distribution of $^{131}$I-Labelled Procine Plasmin in Man and Dog," *Danish Medical Bulletin*,11(5): 146-152 (1964).
Anlyan, W., et al., "Experiences with Fibrinolysin in Peripheral Vascular Occlusive Disease," *Am. J. Cardiol.*, 6: 507-512 (1960).
Barrett, A.J., et al., "The Electrophoretically 'Slow' and 'Fast' Forms of the α2-Macroglobulin Molecule," *Biochem. J.*, 181: 401-418 (1979).
Boucek, R., et al., "Segmental Perfusion of the Coronary Arteries with Fibrinolysin in Man Following a Myocardial Infarction," *Am. J. Cardiol.*, 6: 525-533 (1960).
Boyles, P.W., et al., "Comparative effectiveness of intravenous and intra-arterial fibrinolysin therapy," *Am. J. Cardiol.*, 6: 439-446 (1960).
Castellino, F.J. and J.R. Powell, "Human Plasminogen," *Meth. Enzymology*, 80: 365-378 (1981).
Collen, D., et al., "Thrombolysis with human extrinsic (tissue-type) plasminogen activator in rabbits with experimental jugular vein thrombosis. Effect of molecular form and dose of activator, age of the thrombus, and route of administration," *J. of Clin. Invest.*, 71(2): 368-376 (1983).
Deutsch, D.G. and E.T. Mertz, "Plasminogen: purification from human plasma by affinity chromatography," *Science 170*: 1095-1096 (1970).
Freitag, H., et al., "Lys-plasminogen as an Adjunct to Local Intra-arterial Fibrinolysis of Carotid Territory Stroke: Laboratory and Clinical Findings," *Neuroradiology*, 38: 181-185 (1996).
Hedner, U., et al., "Effects of Porcine Plasmin on the Coagulation and Fibrinolytic Systems in Humans," *Blood*, 51(1): 157-164 (1978).

Kitamoto, Y., et al., "A Femoral Vein Catheter with Immobilized Urokinase (UKFC) as an Antithrombotic Blood Access," *Trans. Am. Soc. Artif. Intern. Organs*, 33: 136-139 (1987).
Larsen, V., "Fibrinolytic Enzyme in the Treatment of Patients with Cancer," *Danish Medical Bulletin*, 2(5): 137-140 (1964).
Larson, V., et al., "Fibrinolytic Treatment with Activator-Free Porcine Plasmin," *Scand. J. Clin. Invest. 18(Suppl. 89)*: 34-73 (1966).
Lijnen, H.R., et al., "Activation of plasminogen by pro-urokinase," *J. Biol. Chem.*, 261(1): 1253-1258 (1986).
Lippschutz, E.L., et al., "Controlled study of the treatment of coronary occulsion with urokinase-activated human plasmin," *Am. J. Cardiol.*, 16 :93-98 (1965).
Moser, K., "Effects of Intravenous Administration of Fibrinolysin (Plasmin) in Man," *Circulation*, 20: 42-55 (1959).
Mizutani et al. "Potential thrombolysis under selective infusion of autolotous plasmin (AP) solution," *Japanese Heart Journal*, 30(5): 723-732 (1989).
Nilsson, T. and B. Wiman, "On the structure of the stable complex between plasmin and alpha-2-antiplasmin," *FEBS Lett.*, 142(1): 111-114 (1982).
Novokhatny, V. et al. "Thrombolytic potential of locally delivered active plasmin (Pm): In vitro assessment and in vivo comparison with tPA in the rabbit jugular vein trombosis model," *Blood, J. of the Am. Soc. of Hematology*, 92(10) Suppl. 2, Abstract 3400. (Nov. 15, 1998).
Robbins, K.C. and L. Summaria, "Plasminogen and Plasmin," *Meth. Enzymol.* 45:257-273 (1976).
Robbins, K.C., et al., Purification of human plasminogen and plasmin by gel filtration on Sephadex and chromatography on Diethylaminoethyl-Sephadex, *The Journal of Biological Chemistry*, 238(3): 952-962 (1963).
Sherry, S., "The Origin of Thrombolytic Therapy," *J. Am. Coll. Cardiol.*, 14(4): 1085-1092 (1989).
Verstraete, M., "The Fibrinolytic System: from Petri Dishes to Genetic Engineering," *Thrombosis and Haemostasis*, 74(1): 25-35 (1995).
Wiman, B., "Affinity-chromatographic purification of human alpha 2-antiplasmin," *Biochem. J.*, 191(1): 229-232 (1980).
Alkjaersig, N., et al., "The Activation of Human Plasminogen," *J. Biol. Chem.*, 233(1): 81-85 (1958).
Alkjaersig, N., et al., "The Mechanism of Clot Dissolution by Plasmin," *J. Clin. Invest.*, 38(7): 1086-1095 (1959).
Becker, Gary, J., "Local Thrombolytic Therapy: Bridging the 'Generation Gap,'" *Am. J. Roentgenol.*, 140(2): 403-405 (1983).
Holmberg, L., et al., "Purification of Urokinase by Affinity Chromatography," *Biochim. Biophys. Acta.*, 445: 215-222 (1976).
Mathey D.G., et al., "Intravenous Urokinase in Acute Myocardial Infarction," *Am. J. Cardiol.*, 55: 878-882 (1985).
Novokhatny, V., et al., "Thrombolytic potency of acid-stabilized plasmin: superiority over tissue-type plasminogen activator in an in vitro model of catheter-assisted thrombolysis," *J. Thromb. Haemost.*, 1: 1034-1041 (2003).
Petitpretz, P., et al., "Effects of a single bolus of urokinase in patients with life-threatening pulmonary emboli: a descriptive trial," *Circulation*, 70(5): 861-866 (1984).
Seifert, V., et al., "Efficacy of Single Intracisternal Bolus Injection of Recombinant Tissue Plasminogen Activator to Prevent Delayed Cerebral Vasospasm after Experimental Subarachnoid Hemorrhage," *Neurosurgery*, 25(4): 590-598 (1989).
Wiman, B., and Per Wallén, "Activation of Human Plasminogen by an Insoluble Derivative of Urokinase Structural Changes of Plasminogen in the course of Activation to Plasmin and Demonstration of a Possible Intermediate Compound," *Eur. J. Biochem.*, 36(1): 25-31 (1973).
Extended European Search Report (EP 1 956 082 A1, dated Jul. 10, 2008).

* cited by examiner

Coomassie Stained Reduced SDS-PAGE (10-20% Tris-Glycine) of CCI Extract, Filtrates and UF/DF Retentate Coomassie-Stained Reduced SDS-PAGE (10-20% Tris-Glycine) of Lysine-Sepharose 4B Affinity Purification of Pmg.

Lysine-Sepharose 4B Chromatogram for the Affinity Purification of Pmg.

Coomassie Stained Reduced SDS PAGE (10-20% Tris, Glycine) of Lysine-Sepharose 4B Eluate (Pmg). pH adjusted from 3.4 to 7.5 in the presence or absense of EACA.

Lane:
1 MW Marker
2 Lys-Seph Eluate; pH 3.4 to 7.5 without EACA
3 Lys-Seph Eluate; ph 3.4 to 7.5 with 20 mM EACA Streptokinase Activation Solution Stability Following 0.5 M NaCl, 0.25M e-ACA stop.

Pmg
Pm HC
Clipped Pm
Pm LC

Lane:
1 = SK Activation Mixure
2 = Unbound Protein
3 = 1 M ε-ACA pH 7.5 Elution
4 = 1 M ε-ACA pH 7.5 Elution pH Adjusted to 3.4
5 = pH 3.0 Column Strip Coomassie-Stained Reduced SDS-PAGE (10-20% Tris-Glycine) of Benzamidine-Sepharose 6B Affinity Purification of Pm.

*Fig. 9*

Hydrophobic Interaction Chromatography
(Octyl-Sepharose 4 FF) Chromatogram
for the Removal of Streptokinase.

PROCESS FOR THE PRODUCTION OF A REVERSIBLY INACTIVE ACIDIFIED PLASMIN COMPOSITION

This is a continuation-in-part of U.S. application Ser. No. 10/143,156, filed May 10, 2002, itself a continuation of International Application PCT/US00/42143 filed Nov. 13, 2000 and published in English on May 25, 2001, itself a continuation-in-part of U.S. application Ser. No. 09/438,331, filed Nov. 13, 1999 (now U.S. Pat. No. 6,355,243, issued Mar. 12, 2002).

FIELD OF THE INVENTION

The present invention relates generally to a method of producing plasmin and more particularly to a method of purifying and isolating the plasmin under conditions which stabilize against degradation.

BACKGROUND

Fibrin is a white insoluble fibrous protein formed from fibrinogen by the action of thrombin. In the clotting of blood, fibrin forms the structural scaffold of a thrombus, which is a clot of blood formed within a blood vessel that remains attached to its place of origin. Under normal conditions the blood clotting system is maintained in equilibrium and the fibrin deposits are dissolved by the fibrinolytic enzyme system. Unfortunately, events such as vascular damage, activation/stimulation of platelets, and activation of the coagulation cascade may disturb the equilibrium, which can result in thrombosis or the blockage of a blood vessel by a blood clot.

Intravascular thrombosis is one of the most frequent pathological events accounting for greater than 50% of all deaths as well as a variety of other serious clinical problems. Most spontaneously developing vascular obstructions are due to the formation of intravascular blood clots, also known as thrombi. Small fragments of a clot may detach from the body of the clot and travel through the circulatory system to lodge in distant organs and initiate further clot formation. Myocardial infarction, occlusive stroke, deep venous thrombosis (DVT) and peripheral arterial disease are well-known consequences of thromboembolic phenomena.

Plasminogen activators are currently the favored agents employed in thrombolytic therapy, all of which convert plasminogen to plasmin and promote fibrinolysis by disrupting the fibrin matrix (M. A. Creager and V. J. Dzau, Vascular Diseases of the Extremities, ppgs. 1398-1406 in Harrison's Principles of Internal Medicine, 14$^{th}$ ed., Fauci et al, editors, McGraw-Hill Co., New York, 1998; the contents of which is incorporated herein by reference in its entirety).

The most widely used plasminogen activators include a recombinant form of tissue-type plasminogen activator (tPA), urokinase (UK) and streptokinase (SK), as well as a new generation of plasminogen activators selected for improved pharmacokinetics and fibrin-binding properties. All of these plasminogen activators, however, by virtue of their mechanism of action, act indirectly and require an adequate supply of their common substrate, plasminogen, at the site of the thrombus to effect lysis.

UK and tPA convert plasminogen to plasmin directly by cleaving the Arg$^{560}$-Val$^{561}$ peptide bond. The resulting two polypeptide chains of plasmin are held together by two interchain disulfide bridges. The light chain of 25 kDa carries the catalytic center and is homologous to trypsin and other serine proteases. The heavy chain (60 kDa) consists of five triple-loop kringle structures with highly similar amino acid sequences. Some of these kringles contain so-called lysine-binding sites that are responsible for plasminogen and plasmin interaction with fibrin, α2-antiplasmin or other proteins. SK and staphylokinase activate plasminogen indirectly by forming a complex with plasminogen, which subsequently behaves as a plasminogen activator to activate other plasminogen molecules by cleaving the arginyl-valine bond.

Although thrombolytic drugs, such as tissue plasminogen activator (tPA), streptokinase, and urokinase, have been successfully employed clinically to reduce the extent of a thrombotic occlusion of a blood vessel, it appears that serious limitations persist with regard to their use in current thrombolytic therapy. For example, because the activation of plasminogen by tPA is fibrin dependent for full proteolytic activity to be realized (Haber et al. 1989), excessive bleeding may result as a side effect of its use. Other adverse sequelae associated with the use of these thrombolytic agents include myocardial infarction, occlusive stroke, deep venous thrombosis and peripheral arterial disease.

Additionally, the known plasminogen activators currently used suffer from several limitations that impact their overall usefulness in the elimination of a thrombus. For example, at best, the use of current thrombolytic therapy results in restored vascular blood flow within 90 min in approximately 50% of patients, while acute coronary re-occlusion occurs in roughly 10% of patients. Coronary recanalization requires on average 45 minutes or more, and intracerebral hemorrhage occurs in 0.3% to 0.7% of patients. Residual mortality is at least 50% of the mortality level in the absence of thrombolysis treatment.

A different approach to avoid the problems associated with the systemic administration of a plasminogen activator to generate sufficient plasmin at the site of the thrombus, is to directly administer the plasmin itself to the patient.

In U.S. Pat. No. 5,288,489, Reich et al., disclose a fibrinolytic treatment that includes parenterally introducing plasmin into the body of a patient. The concentration and time of treatment were selected to be sufficient to allow adequate active plasmin to attain a concentration at the site of an intravascular thrombus that is sufficient to lyse the thrombus or to reduce circulating fibrinogen levels. However, the necessity of generating the plasmin from plasminogen immediately prior to its introduction into the body is also disclosed.

In contrast, U.S. Pat. No. 3,950,513 to Jenson teaches that plasmin compositions may be stabilized at pH 7.0 by including a physiological non-toxic amino acid. This method dilutes stock plasmin solutions stored at low pH with the neutralizing amino acid immediately prior to administration. There are advantages, however, in maintaining low pH of the plasmin composition as long as possible to minimize autodegradation. Ideally, the plasmin will be retained at a low pH until encountering the target fibrin.

Yago et al. disclose plasmin compositions useful as a diagnostic reagent in U.S. Pat. No. 5,879,923. The compositions of Yago et al. comprise plasmin and an additional component which may be 1) an oligopeptide comprising at least two amino acids, or 2) at least two amino acids, or 3) a single amino acid and a polyhydric alcohol. However, the compositions of Yago et al. are formulated at a neutral pH to maintain the enzymatic activity of plasmin.

Plasmin as a potential thrombolytic agent has numerous technical difficulties. These difficulties include the challenge of preparing pure plasmin that is free of all functional traces of the plasminogem activator used to convert plasmin from its inactive precursor, plasminogen. Preparations of plasmin are typically extensively contaminated by plasminogen activator, streptokinase or urokinase and the thrombolytic activity was, therefore, attributed to the contaminating plasminogen activators rather than to plasmin itself. The contaminating plasminogen activators could also trigger systemic bleeding other than at the targeted site of thrombosis. A drawback of streptokinase containing plasmin preparations is that streptokinase can cause adverse immune reactions including fever and anaphylactic shock.

One of the more important technical factors limiting clinical use of plasmin is that plasmin, as a serine protease with broad specificity, is highly prone to autodegradation and loss of activity. This circumstance provides severe challenges to the production of high-quality plasmin, to the stable formulation of this active protease for prolonged periods of storage prior to use, and to safe and effective administration of plasmin to human patients suffering from occlusive thrombi. Thus, there is need for a method of producing stable plasmin.

SUMMARY

The present invention provides for both a process for producing a reversibly inactive acidified plasmin by activating plasminogen and a process for producing a purified plasminogen. The produced plasmin is isolated and stored in a low pH, low buffering capacity agent to provide a substantially stable formulation. The purified plasminogen is typically purified from a fraction obtained in the separation of immunoglobulin from Cohn Fractions II+III. (see, e.g., Cohn, E. J., et al., *J. Amer. Chem. Soc.*, 68:459 (1946); E. J. Cohn, U.S. Pat. No. 2,390,074; and Oncley, et al., *J. Amer. Chem. Soc.*, 71:541 (1949), the entire disclosures of which are hereby incorporated by reference herein) by affinity chromatography with an elution at a low pH. The reversibly inactive acidified plasmin may be used in the administration of a thrombolytic therapy.

Briefly, the method for purifying plasmin comprises cleaving a plasminogen in the presence of a plasminogen activator to yield an active plasmin and removing the plasminogen activator from the active plasmin to form a plasmin solution. A low pH, low buffering capacity agent can then be added to the final plasmin solution to form a reversibly inactive acidified plasmin. The final plasmin solution may be buffered to a pH of between about 2.5 to about 4.

The plasminogen activator can be removed from the active plasmin by binding the active plasmin to an active plasmin-specific absorbent material to form a bound plasmin. One such active plasmin-specific absorbent material can comprise benzamidine. Once bound, the active plasmin can be eluted with a low pH solution to form a final plasmin solution. Plasminogen activator may also be further removed by hydrophobic interaction.

A further method of purifying plasmin comprises cleaving plasminogen to yield an active plasmin and binding the active plasmin to an active plasmin-specific absorbent material to form a bound plasmin. The bound plasmin can be eluted with a substantially neutral pH solution to form a final plasmin solution which is substantially free of degraded plasmin. The substantially neutral pH solution can comprise excipients such as omega-amino acids and salts that are typically filtered out or otherwise removed from the final plasmin. The final plasmin may also be buffered with a low pH, low buffering capacity agent.

The process for the purification of plasminogen from a plasma source includes the steps of adding the plasminogen containing solution to a plasminogen-specific absorbent material and then eluting the plasminogen from the plasminogen-specific absorbent material at a pH of between about 1 to about 4. The purified plasminogen is then collected as an eluate. Additionally, the process may include methods for the purification of micro- or mini-plasmin(ogen) or other truncated or modified forms of plasmin(ogen).

Thus, a process is now provided that successfully addresses the shortcomings of existing processes and provides distinct advantages over such processes. Additional objects, features, and advantages of the invention will become more apparent upon review of the detailed description set fourth below when taken in conjunction with the accompanying drawing figures, which are briefly described as follows.

BRIEF DESCRIPTION OF THE FIGURES

FIG. 9 depicts a Coomassie stained reduced SDS-PAGE (10-20% Tris-Glycine) of benzamidine SEPHAROSE 6B purified Pm;

DETAILED DESCRIPTION

Figure 1:
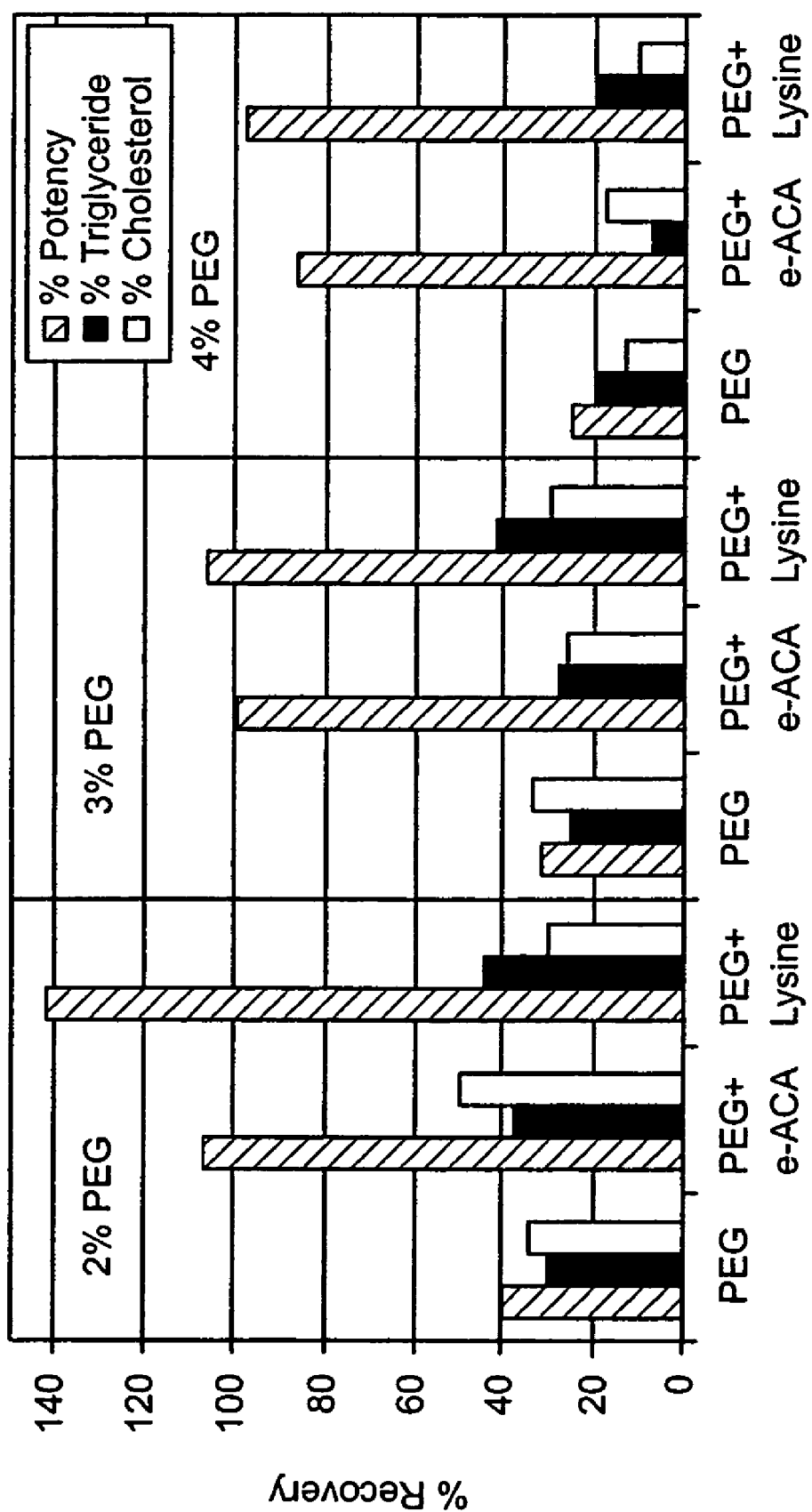
FIG. 1 graphically depicts the effect of lysine derivatives on plasminogen recovery and lipid removal from CCI filtrate I through polyethylene glycol (PEG) precipitation/depth filtration.

The present invention comprises both a method for producing a reversibly inactive acidified plasmin in combination with low pH, low buffering capacity agent and a method for the purification of plasminogen from a plasma source. The inactive acidified plasmin solution may also include a stabilizer in addition to being inactivated in buffered solution. The process for purifying plasminogen provides for both inactivation and removal of pathogens and the elution of the plasminogen at a low pH. The inactive acidified plasmin preparation can be used in the administration of a thrombolytic therapy.

Purification of Plasminogen

The present invention includes both a process for the purification of plasminogen and plasmin and concurrently, methods for the inactivation and removal of viral and Transmissible Spongiform Encephalopathies (TSE) contaminants during these processes. The terms "TSE" or "TSE contaminants" and "pathogenic prion protein" are used interchangeably herein unless specifically noted. The starting material, plasminogen, can be purified from Cohn Fraction II+III paste by affinity chromatography on Lys-SEPHAROSE as described by Deutsch, D. G. and E. T. Mertz, "Plasminogen: purification from human plasma by affinity chromatography," *Science* 170(962):1095-6 (1970).

SEPHAROSE is a trade name of Pharmacia, Inc. of New Jersey for a beaded form of agarose gel, a high molecular weight substance for the separation by gel filtration of macromolecules. The process may be performed on any plasma source, recombinant source, cell culture source or transgenic source. For example, plasma from a waste fraction derived from the purification of immunoglobulin from a chromatographic process can be used as described in commonly owned U.S. patent application Ser. No. 09/448,771, filed Nov. 24, 1999, which is incorporated by reference herein.

Plasminogen was extracted from this waste fraction (referred to herein as the "caprylate cake I" (CCI)) over a wide range of pH. Conditions of extraction can be varied from a pH of about 3.5 to about 10.5 using a variety of buffers capable of providing a pH in this range, including citrate, acetate, tris, imidazole, histadine, HEPES and/or phosphate buffers. The extraction can occur at temperatures from about 4° C. to 37° C. and can be run for 1 to 24 hours without deleterious effect. In addition, the ionic strength can be varied by the addition of about 0.2 Molar sodium chloride without deleterious effect on the extraction of plasminogen.

Following the extraction of plasminogen, lipid and protein impurities and TSE were reduced by precipitation with the addition PEG, in a range of about 1 to about 10% weight/volume or the addition of about 80 to about 120 g/L ammonium sulfate. The PEG or ammonium sulfate precipitate can be removed by depth filtration. The resulting solution is then placed on a lysine affinity resin column.

Removal of lipid and protein impurities above can be further enhanced by the addition of a particulate metal oxide. The metal oxide can be silicon dioxide or aluminum hydroxide. The metal oxide can also be fumed alumina. The silicon dioxide can be a fumed silica. The fumed silica can be a fumed silica filter-aid such as CAB-O-SIL® M-5P fumed silica from Cabot Corporation, Tuscola, Ill. (an amorphous, colloidal silicon dioxide). Use of a particulate metal oxide can result in a significant further reduction in lipids and proteinaceous contaminants such as TSE pathogenic prion proteins. Use of a fumed silica filter aid, e.g. CAB-O-SIL, has been shown to result in a further reduction of prion proteins of from about 2 to about 3 logs, in addition to the clearance effect of PEG. See FIG. 12 and Example 14 below.

If desired, the solubility of plasminogen may be enhanced by the addition of excipients, e.g., omega-amino acids (lysine, polylysine, arginine, tranexamic acid, or epsilon amino caproic acid, or combinations or analogues thereof). Solubility enhancement may be accomplished with from about 0.02 M to about 1 M of a suitable excipient. Preferably about 0.2 M lysine is sufficient. If added, the lysine is preferably removed by diafiltration (after the PEG, fumed silica (e.g. CABOSIL), cation-exchange column chromatography, and/or ammonium sulfate precipitation and depth filtration), and the resulting solution placed on a lysine affinity resin column. The phrase "lysine affinity resin" is used generally for affinity resins containing lysine or its derivatives or epsilon caproic acids as the ligand. The column can be eluted with a low pH solution of approximately 1 to 4.

The protein obtained after elution from the affinity column is generally at least 80% plasminogen. The purified plasminogen is then stored at low pH in the presence of simple buffers such as glycine and lysine or omega-amino acids. Storage at low pH also provides an opportunity for viral inactivation and removal and TSE removal as determined by spiking methods. The studies of the present invention suggest that plasmin meets the most stringent requirements for 6 log clearance of non-enveloped viruses including one 4 log removal step, and 10 log clearance for enveloped viruses including two orthogonal 4 log elimination steps. In addition to sufficient virus clearance, the plasmin process of the invention is characterized by greater than 6 logs of TSE infectivity removal for added safety.

The plasminogen in solution is then activated to plasmin by the addition of a plasminogen activator, which may be accomplished in a number of ways including but not limited to streptokinase, urokinase, or the use of urokinase immobilized on resin and use of streptokinase immobilized on resin. The preferred plasminogen activator is soluble streptokinase. The addition of stabilizers or excipients such as glycerol, omega-amino acids such as lysine, polylysine, arginine, epsilon amino caproic acid and tranexamic acid, and salt enhance the yield of plasmin.

Purifying Plasmin

Plasmin was purified from unactivated plasminogen by affinity chromatography on resin with benzamidine as the ligand and eluted with a neutral pH excipient solution or low pH solution. This step can remove essentially all degraded plasmin as well as the majority of the streptokinase.

As a polishing step for the removal of remaining streptokinase, hydrophobic interaction chromatography (HIC) at low pH is performed. Following the HIC step, the plasmin is formulated as a sterile protein solution by ultrafiltration and diafiltration and 0.22 μm filtration.

The present method additionally includes the steps of activating plasminogen to plasmin using a plasminogen activator and then capturing the formed active plasmin on an active plasmin-specific absorbent material. The bound plasmin is then eluted with a low pH buffer. The eluted plasmin is buffered with a low pH, low buffering capacity agent such as an acid. Typically, the eluted plasmin is buffered to a pH of between about 2.5 to about 4.

The low buffering capacity of the acidic buffer allows the reversibly inactivated acidified plasmin to be brought up to physiological pH quickly, becoming activated thereby when administered as a thrombolytic agent. Typically, the buffer is added in a concentration at which the pH of the acidified plasmin is raised to neutral pH by adding serum in an amount no more than about five times the volume of the acidified plasmin.

Cleaving the Plasminogen to Yield an Active Plasmin

Plasminogen can be cleaved to plasmin by using a catalytic concentration of an immobilized or soluble plasminogen activator. Plasmin, the principle fibrinolytic enzyme in mammals, is a serine protease with trypsin-like specificity that is derived from the inactive zymogen precursor plasminogen circulating in plasma. Plasminogen itself is a 790 amino acid polypeptide having an N-terminus glutamate residue. Plasminogen activators such as soluble streptokinase, tissue plasminogen activator (tPA) or urokinase will cleave the single-chain plasminogen molecule to produce active plasmin at the Arg560-Val561 peptide bond. The resulting two polypeptide chains of plasmin are held together by two interchain disulfide bridges. The light chain of 25 kDa carries the catalytic center and is homologous to trypsin and other serine proteases. The heavy chain (60 kDa) consists of five triple-loop kringle structures with highly similar amino acid sequences.

Some of these kringles contain so-called lysine-binding sites that are responsible for plasminogen and plasmin interaction with fibrin, α2-antiplasmin or other proteins.

The activation of plasminogen can occur at about 4° C. to about 37° C. and typically takes between about 2 to 24 hours. The plasminogen can be cleaved in the presence of stabilizers or excipients such as omega-amino acids, salts, and glycerol. The omega-amino acids can include lysine, epsilon amino caproic acid, tranexamic acid, poly lysine, arginine and combinations or analogues thereof. Upon the completion of the activation, the plasmin solution can be filtered and further stabilized for several days at neutral pH by the addition of excipients such as omega-amino acids and sodium chloride and applied to benzamidine-SEPHAROSE.

Removing Plasminogen Activator and Impurities

The active plasmin formed from the cleaving of the plasminogen can then be bound to an active plasmin specific absorbent to substantially remove the plasminogen activator. Because the protein of interest is an active serine protease with trypsin-like specificity, benzamidine may be used as an active plasmin specific absorbent that allows for the capture of the active plasmin. Other active plasmin specific absorbents having similar properties as benzamidine may also be used. The benzamidine can be immobilized in a solid support medium. The solid support medium can be a resin or SEPHAROSE. Additionally, hydrophobic interaction may be used to further remove the plasminogen activator (see below, Removal of Streptokinase by Hydrophobic Interaction Resin Chromatography).

More specifically, the cleaved plasminogen is typically contained in a solution of amino acids, sodium chloride and glycerol, which allows for stability of the solution for several days at neutral pH before it is applied to a benzamidine-SEPHAROSE column equilibrated with about 0.05 M Tris, pH 8.5, 0.5 M NaCl. The column is typically run at 4° C. The front portion of the non-bound peak contains high-molecular weight impurities, with the rest of the non-bound peak being represented by residual non-activated plasminogen and by inactive autodegradation products of plasmin.

The bound plasmin can then be eluted with an acid buffer or with a substantially neutral pH excipient solution. The plasmin bound to benzamidine-SEPHAROSE can be eluted with an acidic buffer such as glycine buffer. When a substantially neutral pH excipient solution is used to elute the bound plasmin, the final eluted plasmin solution can be substantially free of degraded plasmin. Typically, the substantially neutral pH excipient solution has a pH of value of between about 6.5 to about 8.5. However, the pH of the solution can range from about 2.5 to about 9.0. In particular embodiments, the pH can be from about 4.0 to about 7.5. In other embodiments, the pH can be about 6.0. Examples of excipients include omega-amino acids, including lysine, epsilon amino caproic acid, tranexamic acid, polylysine, arginine, and analogues and combinations thereof, and salts such as sodium chloride.

An appropriate concentration of salt can be represented by a conductivity from about 5 mS to about 100 mS. Generally, the salt concentration can be varied somewhat inversely in relation to acidity, i.e. lower pH solutions can work well with lower salt and solutions having higher pH (within the ranges discussed above) can work well with higher salt concentrations. When the salt is sodium chloride, the concentration can be from about 50 mM to about 1000 mM, or from about 100 mM to about 200 mM. When the solution is at about pH 6.0, the concentration of sodium chloride can be about 150 mM.

Removal of Streptokinase by Hydrophobic Interaction Resin Chromatography

As noted above, the streptokinase activator may be further removed from plasmin by hydrophobic interaction chromatography. In particular embodiments, the activated plasmin solution is made about 0.1 M in ammonium sulfate and subjected to hydrophobic interaction chromatography, e.g. in a column format using a resin such as octyl-SEPHAROSE.

Nanofiltration of Plasmin

The octyl-SEPHAROSE flow-through containing active plasmin can be subjected to nanofiltration. The flow-through is generally subjected to pre-filtration with a 0.1 micron filter capsule, and then subjected to nanofiltration, e.g. using an ASAHI NF (normal flow) 1.0 $m^2$ 15N membrane (PL-ANOVA filters, Asahi Kasei America, Inc., Buffalo Grove, Ill.). Implementing nanofiltration further downstream in the process, after octyl hydrophobic interaction chromatography, improves throughput and membrane flux properties due to a more pure feedstream.

Buffering the Plasmin Solution with a Low pH, Low Buffering Capacity Agent

The eluted plasmin can be buffered with a low pH, low buffering capacity agent. The low pH, low buffering capacity agent typically comprises a buffer of either an amino acid, a derivative of at least one amino acid, an oligopeptide which includes at least one amino acid, or a combination of the above. Additionally the low pH, low buffering capacity agent can comprise a buffer selected from acetic acid, citric acid, hydrochloric acid, carboxcylic acid, lactic acid, malic acid, tartaric acid, benzoic acid, serine, threonine, methionine, glutamine, alanine, glycine, isoleucine, valine, alanine, aspartic acid, derivatives or combinations thereof. The buffer can be present in the reversibly inactive acidified plasmin at a concentration such that the pH of the acidified plasmin can be raised to neutral pH by adding serum to the composition in an amount no more than about 4 to 5 times the volume of acidified plasmin.

The concentration of plasmin in the buffered solution can range from about 0.01 mg/ml to about 50 mg/ml of the total solution. The concentration of the buffer can range from about 1 nM to about 50 mM. Of course, these ranges may be broadened or narrowed depending upon the buffer chosen, or upon the addition of other ingredients such as additives or stabilizing agents. The amount of buffer added is typically that which will bring the reversibly inactive acidified plasmin solution to have a pH between about 2.5 to about 4.

Further Stabilizing the Inactive Acidified Plasmin Solution

The reversibly inactive acidified plasmin solution may be further stabilized by the addition of a stabilizing agent such as a polyhydric alcohol, pharmaceutically acceptable carbohydrates, salts, glucosamine, thiamine, niacinamide, or combinations thereof. The stabilizing salts can be selected from the group consisting of sodium chloride, potassium chloride, magnesium chloride, calcium chloride and combinations thereof. Sugars or sugar alcohols may also be added, such as glucose, maltose, mannitol, sorbitol, sucrose, lactose, trehalose, and combinations thereof.

Concentrations of carbohydrate added to stabilize the reversibly inactive acidified plasmin solution include a range from about 0.2% w/v to about 20% w/v. Ranges for a salt, glucosamine, thiamine, niacinamide and their combinations can range from about 0.01 M to about 1 M.

Plasmin formulated formulated according to the invention in buffered acidified water has been found to be extremely stable. It can be kept in this form for months without substantial loss of activity or the appearance of degradation products of a proteolytic or acidic nature. At 4° C., plasmin is stable for at least nine months. Even at room temperature, plasmin is stable for at least two months. Long-term stability at room temperature can allow this formulation to be compatible with long regimens of thrombolytic administration. For example, 36 hours administration of thrombolytics such as tissue plasminogen activator or urokinase is common in treatment of peripheral arterial occlusions.

The ability of a buffered acidified plasmin to become fully active upon transfer to physiological pH is evidenced by its activity in the caseinolytic assay and also in the $I^{125}$-fibrin-labelled clot lysis assays. Both of these assays are performed at pH 7.4, and there was complete recovery of plasmin activity during the change of pH and passing through the iso-pI point (pH 5-5.5). This is because plasmin is formulated in a non-buffered solvent and when added to a buffered solution (either PBS or plasma) it adopts the neutral pH instantly and the precipitation that usually accompanies the slow passage through the iso-pI point, does not occur.

A feature of the active plasmin as used in the present invention is the maintenance of the plasmin in an acidic buffer and its formulation in acidified water, providing a pure and stable active plasmin. Its efficacy was demonstrated in in vitro assays and in an in vivo rabbit jugular vein thrombolysis model unified, substantially purified or partially purified enzyme such as, but not limited to, plasmin or any composition containing plasmin that is within the scope of the present invention.

A description of a method of treating thrombolysis and related ailments employing aspects of the claimed invention is disclosed in the application entitled "Method of Thrombolysis by Local Delivery of Reversibly Inactivated Acidified Plasmin," U.S. patent application Ser. No. 10/143,157, commonly assigned, and incorporated herein by reference in its entirety. Additionally, compositions made in accordance with the claimed invention are disclosed in the application entitled "Reversibly Inactivated Acidified Plasmin," U.S. patent application Ser. No. 10/143,112, and commonly assigned, and incorporated herein by reference in its entirety.

The following examples are given only to illustrate the present process and are not given to limit the invention. One skilled in the art will appreciate that the examples given only illustrate that which is claimed and that the present process is only limited in scope by the appended claims.

EXAMPLES

Example 1

Caprylate Cake I (CCI) Extraction and Lipid Reduction by PEG Precipitation and Filtration Caprylate cake I (CCI) is a fraction resulting from a pH 5 caprylate precipitation of resuspended Cohn Fractions II+III in the IGIV-C process (see, e.g., Lebing, W. et al. *Vox Sang*, 84(3):193-201 (April 2003)). Plasminogen (Pmg) is extracted from the CCI by solubilizing at a cake:buffer ratio of about 1:10 for 2 to 3 hours at 4° C. with mixing. While several extraction solutions were investigated, the current method was performed with 100 mM Tris pH 10.5 to maintain the pH at or above neutral; a condition favorable to Pmg solubilization from the CCI. Table 1 depicts the extraction solutions investigated along with their final extract pH and Pmg potency.

TABLE 1

CCI Extraction Solutions: Resulting Final Extract pHs and Pmg Activities.

| Extraction Solution | Final Extract pH | Pmg (IU/ml) |
|---|---|---|
| 0.1 M Tris pH 10.5 | 9.2-9.5 | 1.77 |
| 0.2 M Tris pH 7.5 | 7.5 | 2.06 |
| 0.05 M Citrate, 0.2 M ε-ACA, 0.4 M NaCl pH 6.5 | 6.0 | 1.49 |
| 0.15 M Citrate pH 8.3 | 6.7 | 1.21 |
| 0.4% Acetic Acid pH 3.5 | 3.5 | 0.05 |

Following 2 to 3 hours of extraction, the temperature of the extract is adjusted to 20° C. and the pH to 7.5. Table 2 shows the Pmg yield, based on nephelometry, from Clarified Plasma Pool through Fraction II+III and CCI Extract.

TABLE 2

Step and Process Yields for Pmg from Clarified Plasma Pool to CCI Extract.

| Cohn Fraction | mg Pmg/g (SD), n | % Pmg Step Yield | % Pmg Process Yield |
|---|---|---|---|
| Clarified Plasma Pool | 0.124 (0.013), 33 | | |
| Fraction II + III | 0.143 (0.024), 30 | 65.6 | |
| CCI Extract (post L-lysine) | 0.145 (0.01), 7 | 101 | 66.3 |

Only about 66% of the Pmg in plasma tracks to Fraction II+III while virtually all of the Pmg found in the resuspended Fraction II+III precipitates to and is extracted from CCI. Extraction of CCI in Tris pH 10.5, final CCI Extract pH of 9.2-9.5, solubilizes all of the Pmg found in the CCI.

The addition of lysine derivatives (100 mM L-lysine, 50 mM epsilon amino caproic acid (EACA)) increases the solubility of Pmg in the CCI Extract resulting in increased recoveries during subsequent PEG precipitation and filtration steps as illustrated in FIG. 1.

Reduction of lipid is achieved through precipitation by the addition of PEG 3350 to 3%-4% w/w. As mentioned previously, the addition of L-lysine to 100 mM prior to PEG addition is necessary to maintain high Pmg recovery in the PEG filtrate, or about 90%. Without the addition of lysine, only about 25% of the Pmg is recovered in the PEG filtrate (FIG. 1). The PEG precipitation proceeds for 1 to 2 hours at 20° C. with mixing. Filter aid is added to 4% w/w and mixed prior to depth filtration through a CUNO 30SP followed by further clarification with 0.5 micron and 0.22 micron filters.

Figure 2:
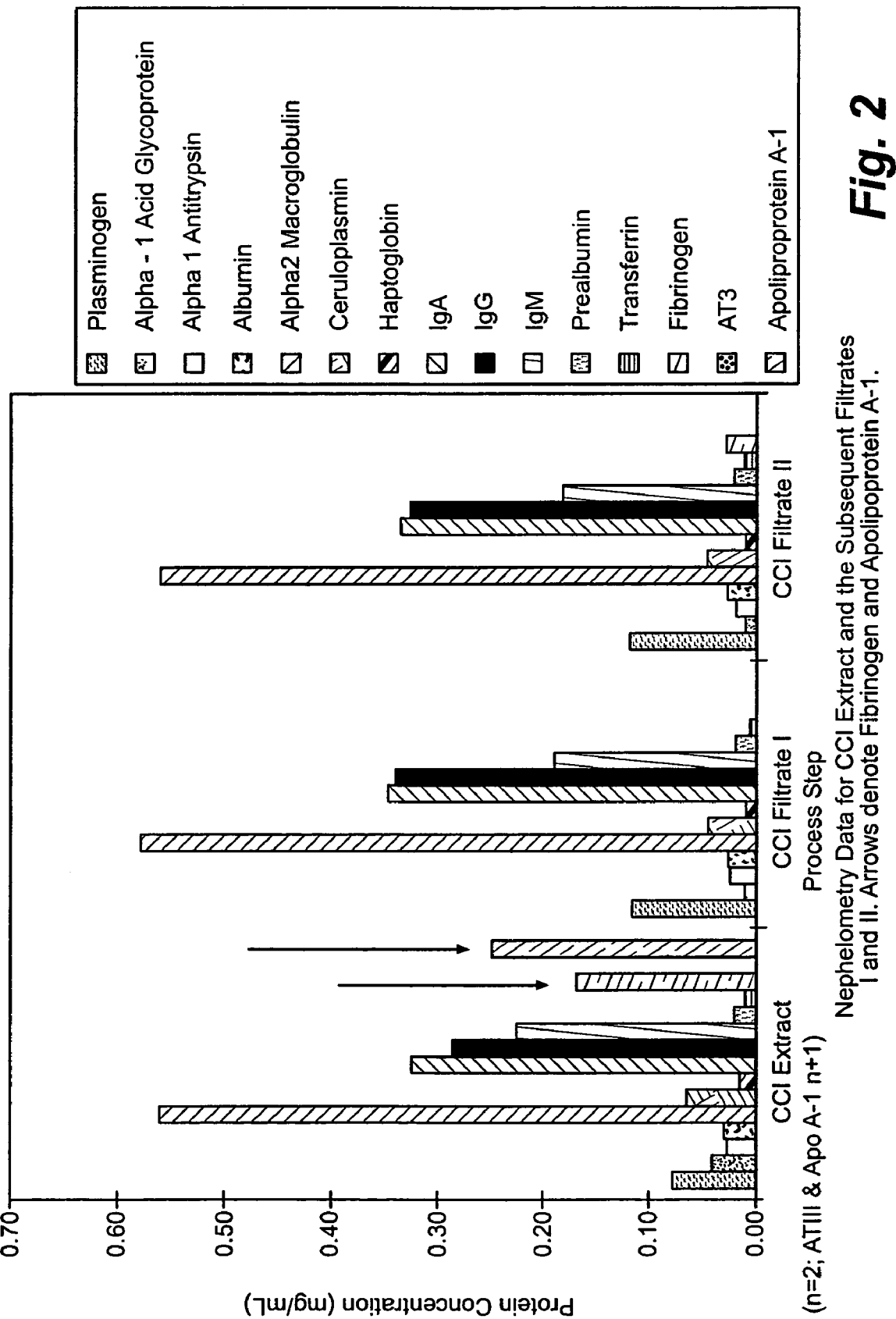
FIG. 2 graphically depicts nephelometry data for CCI extract and the subsequent filtrates I and II.

FIG. 1 shows the lipid content, determined by cholesterol and triglycerides concentration, is reduced by 60-70% following PEG precipitation and filtration (CCI Filtrate I). The CCI Filtrate I is diluted 1:1 with phosphate buffered saline pH 7.5 and held at 20° C. for 1 to 2 hours as precipitation often continues following filtration. The CCI Filtrate I is filtered through 0.5 μm and 0.22 μm filters to remove any additional precipitate; CCI Filtrate II. Nephelometry data for CCI Extract and CCI Filtrates I and II are illustrated in FIG. 2. Note that fibrinogen and apolipoprotein A-1 concentrations are reduced following PEG precipitation.

The CCI Filtrate II is diafiltered by tangential flow filtration (TFF) against phosphate buffered saline pH 7.5 to reduce the L-lysine concentration such that it will not act as a competitive inhibitor for Pmg binding to the lysine affinity resin. Experiments were performed to illustrate the necessity of lysine removal. Loading the CCI Filtrate II directly onto a lysine affinity resin without reduction in soluble lysine concentration, results in the capture and release of about 4% of the Pmg activity. Diluting the CCI Filtrate II 1:1 with TBS (10 mM Tris, 150 mM NaCl pH 7.5) still resulted in capture and release of only about 5% of the Pmg activity. Following 5 volumes of diafiltration to reduce the lysine concentration, about 22% of the Pmg activity was captured and released from the lysine affinity resin (in retrospect, the column was overloaded by about 50%).

Figure 3:
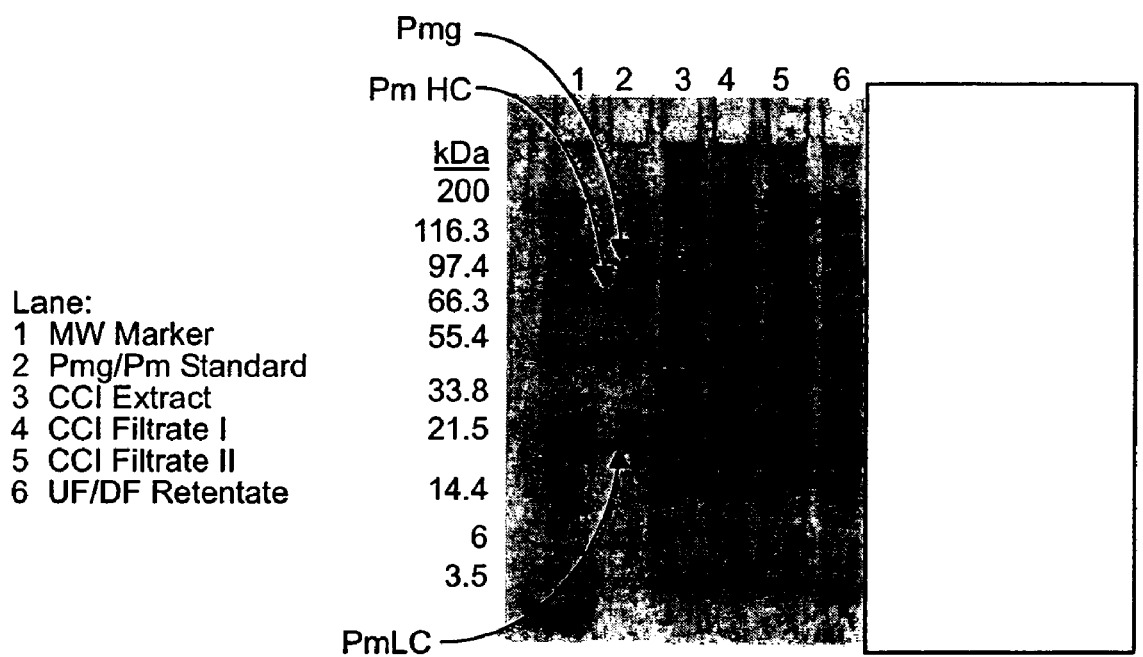
FIG. 3 depicts a gel of Coomassie stained reduced SDS-PAGE (10-20% Tris-Glycine) of CCI extract, filtrates and UF/DF retentate.

Constant volume diafiltration was performed by tangential flow filtration (TEF) against 5 volumes phosphate buffered saline pH 7.5 using a 30 kDa molecular weight cutoff membrane. Following diafiltration, the protein solution was concentrated by ultrafiltration to 4 to 5 $A_{280}$/ml. Pmg recoveries in the UF/DF retentate, by nephelometry, averaged 84% (±1, n=3). FIG. 3 shows reduced SDS PAGE for each of the process intermediates discussed thus far. The data in FIGS. 2 and 3 illustrate the complexity and heterogeneity of the CCI Extract and subsequent Filtrates.

Example 2

Figure 4:
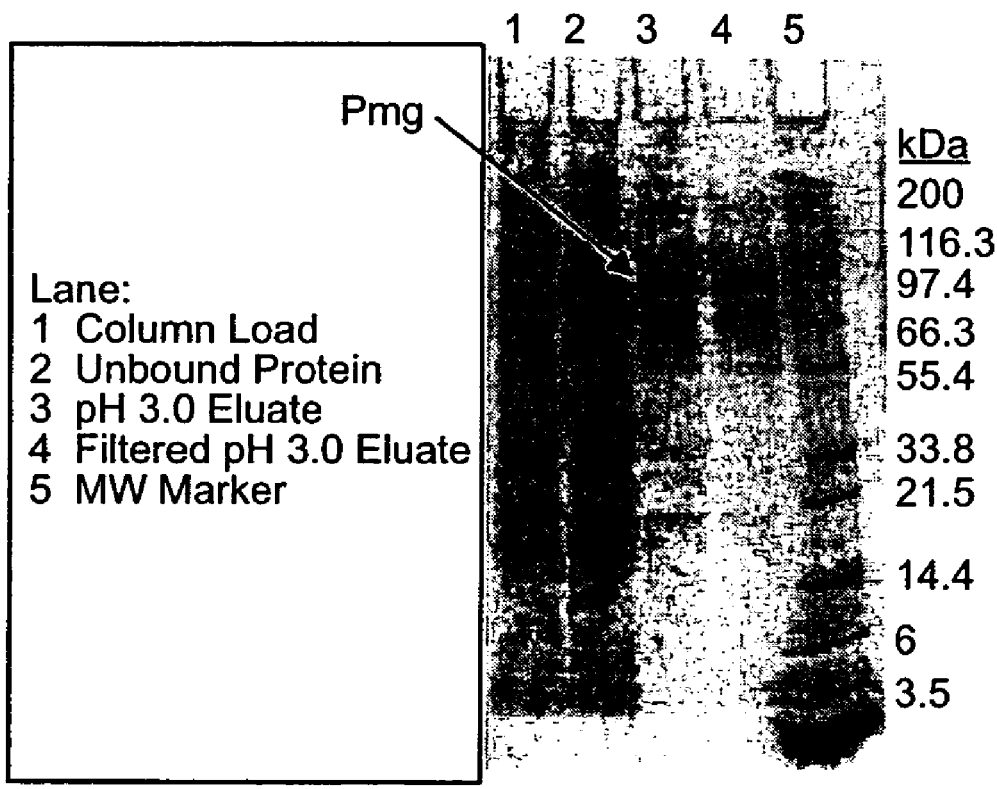
FIG. 4 depicts a Coomassie stained reduced SDS-PAGE (10-20% Tris-Glycine) of lysine SEPHAROSE 4B affinity purification of Plasminogen (Pmg)
Figure 5:
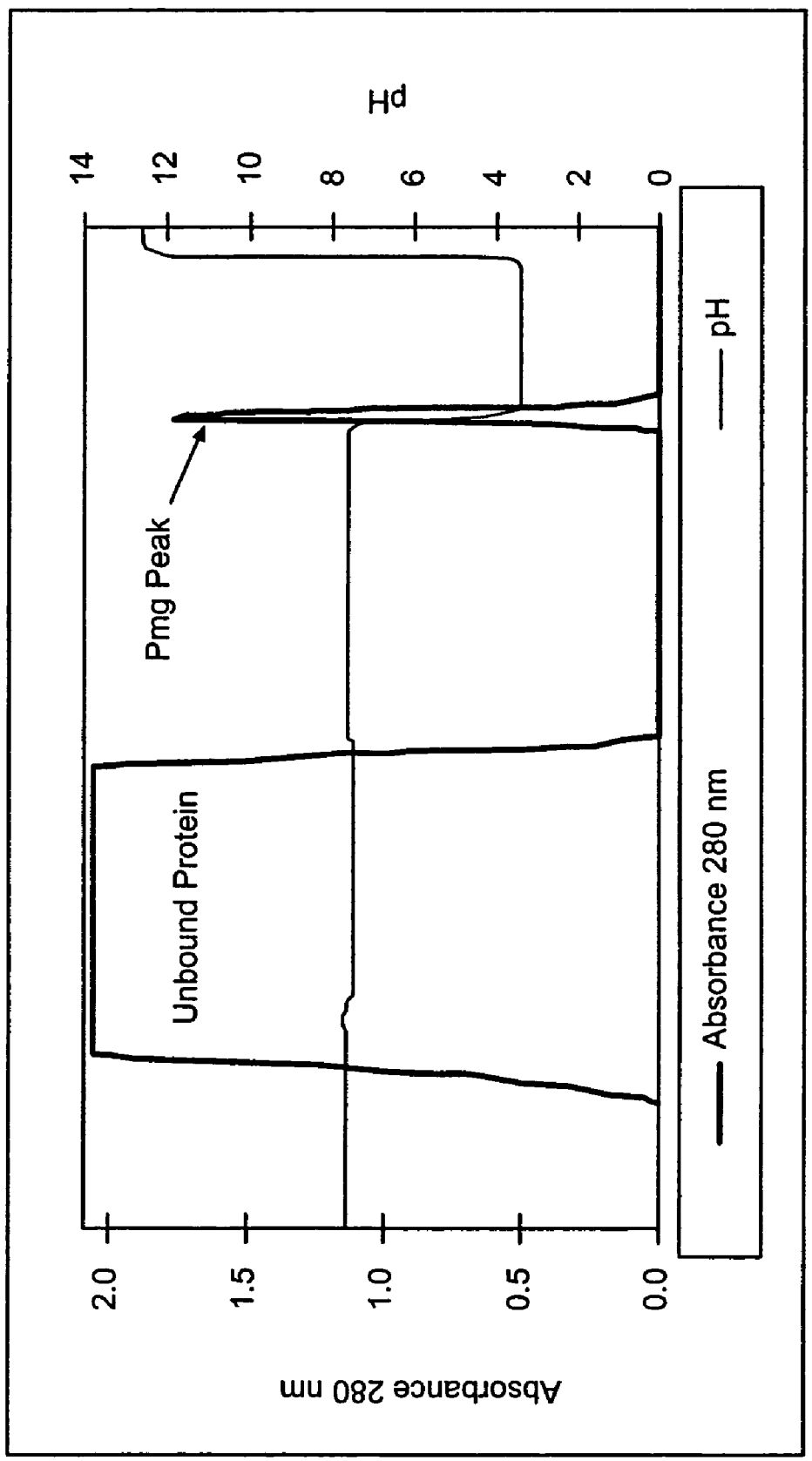
FIG. 5 graphically depicts a lysine SEPHAROSE 4B chromatogram for the affinity purification of Pmg.

Purification of Pmg by Lysine Affinity Chromatography:

The purpose of lysine affinity chromatography is to purify Pmg, which represents from about 3 to 5% of the total protein in the diafiltered CCI Filtrate II. The DF CCI Filtrate II was applied to a Lysine-SEPHAROSE 4B (Amersham Pharmacia #17-0690-01) column equilibrated with 0.01 M $NaH_2PO_4$, 0.15 M NaCl pH 7.5, at 3.5-4.0 $A_{280}$/ml resin. Unbound proteins were washed through the column with the equilibration buffer and the resin was then washed with 0.01 M $NaH_2PO_4$, 0.5 M NaCl pH 7.5 to remove non-specifically bound protein; no protein was removed. Bound protein, Pmg, was eluted with 0.1 M Glycine, 0.03 M Lysine pH 3.0 and collected with mixing to maintain low pH. FIGS. 4 and 5 show SDS PAGE analysis and the chromatogram of the lysine affinity purification of Pmg, respectively. The resin was cleaned sequentially with 0.1 N NaOH and 2.0 M NaCl, 0.1% Triton X-100 and stored in 20% ethanol. Table 3 shows Pmg step yield by nephelometry and purity by reduced SDS PAGE.

TABLE 3

Lysine Affinity Chromatography Pmg Step Yield and Purity

| Process Intermediate | Step Yield % | Pmg Purity % |
|---|---|---|
| Lysine-SEPHAROSE 4B Eluate | 75.7 | 85.9 |

Example 3

Viral Inactivation and Removal and TSE Removal

Nanofiltration

The optimal placement of a nanofiltration step during the Plasmin process, along with determining the optimal conditions for pathogens removal from Pmg lysine affinity eluate (Pmg) for a particular nanofiltration scheme was tested. Pmg was spiked with porcine parvovirus (PPV) or bovine diarrhea virus (BVDV) and filtered through a PALL DV20 filter membrane. All runs were performed with 50 ml starting material (0.3 mg/ml Pmg), 30 psi constant pressure, pH 3.4 and room temperature. The challenge solution was pre-filtered through 0.22 µm prior to nanofiltration. The determining factors for the optimal conditions for removal of different pathogens by nanofiltration deal mainly with the attainment of a minimum of 4 log infectivity removal of known pathogens, percent product recovery, percent potency remaining, product concentration and product pH. It was found that PPV and BVDV clearance was >4 $log_{10}$ $TCID_{50}$. The nanofiltration step has also the capability of removing greater than 4 log of TSE. All product recoveries obtained in the study were ≧95% with no substantial change in Pmg activity.

Caprylate Viral Inactivation.

Because caprylate inactivation is very much pH dependent and more efficacious under acidic pH conditions, virus inactivation by caprylate at the low pH lysine affinity chromatography elution step was examined. BVDV was used as a model enveloped virus to study caprylate virucidal activity in lysine affinity eluate. Complete BVDV inactivation, resulting in ≧4.4 $log_{10}$ reduction, was detected at the lysine affinity column eluate with 3 mM caprylate at pH 3.4 during 30 min of incubation at room temperature in the presence of 1.5 mg/ml Pmg. In the absence of product, complete BVDV inactivation (≧4.7 $log_{10}$ reduction) was also achieved with 3 mM caprylate after 30 minutes at pH 3.4. No visible precipitation was observed during the caprylate treatment suggesting that the product and virus spike remain soluble and are not being precipitated by the caprylate. The impact of the added caprylate on product recovery or potency following lysine affinity column chromatography was minimal.

PEG Precipitation

The effect of PEG on TSE removal was investigated. The clarification and removal of lipids achieved by depth filtration and 3% PEG precipitation of the Caprylate Cake I Extract resulted in greater than 2 $log_{10}$ of TSE removal.

TABLE 4

Total Virus/TSE clearance across Plasmin process

| Step | BVDV | PPV | TSE |
|---|---|---|---|
| Nanofiltration | >4 log | 4 log | 4 log |
| 3 mM Caprylate | >4 log | <1 log | <1 log |
| Lysine Affinity | 3.3 log | 2.5 log | pending |
| PEG precipitation | <1 | <1 | 2-3 logs |
| Total clearance | >12 | >6 | >6 |

Example 4

Figure 6:
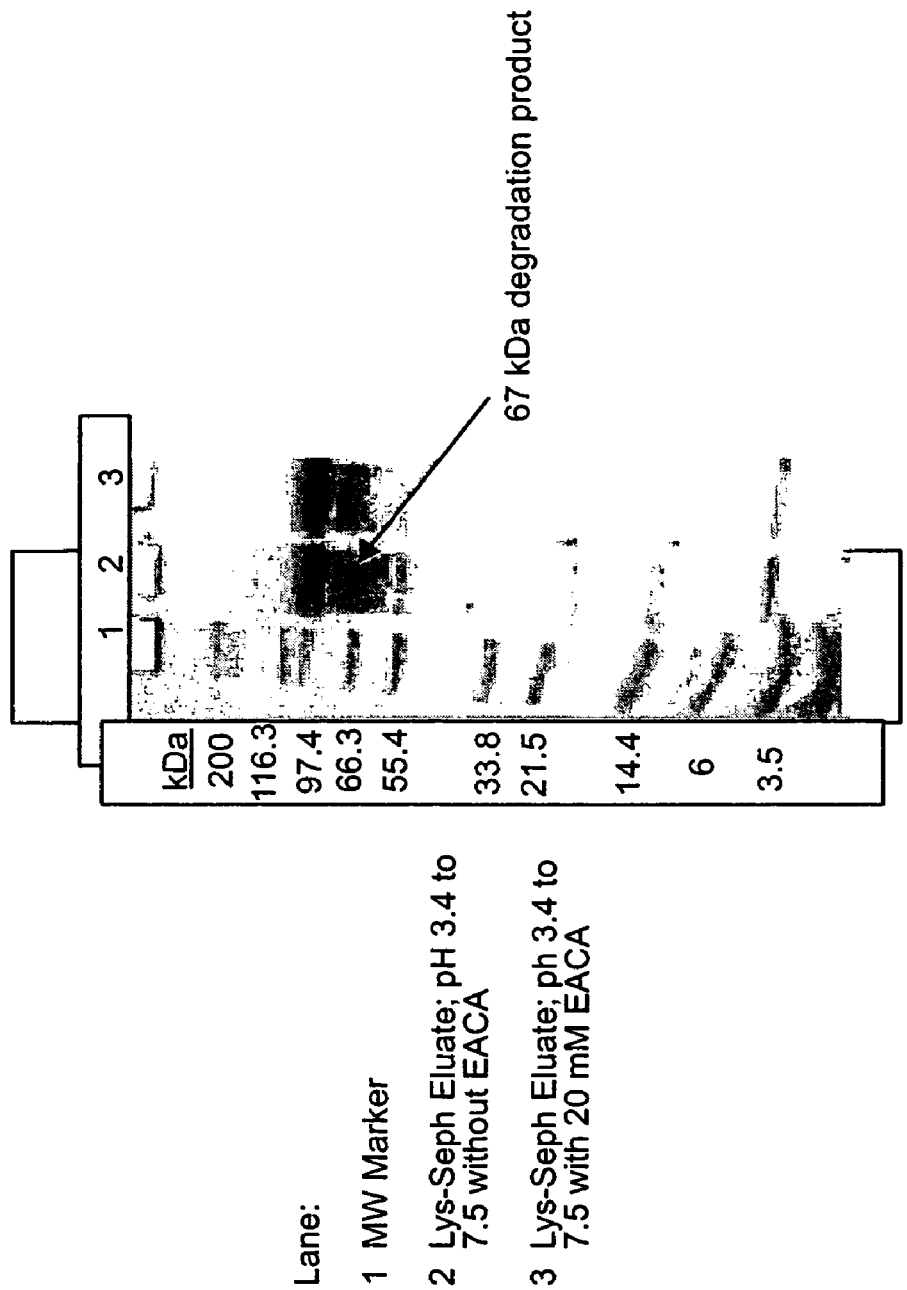
FIG. 6 depicts a Coomassie stained reduced SDS-PAGE (10-20% Tris-Glycine) of pH adjustment of the lysine SEPHAROSE 4B eluate (Pmg) with and without epsilon amino caproic acid ($\epsilon$-ACA or EACA) present.

Streptokinase (SK) Activation of Pmg to Pm (Pm):

The addition of SK to the purified Pmg solution effects the conversion of Pmg to Pm. The lysine affinity column eluate pH 3.4 is concentrated by TFF to 2 mg/ml through a 30 kD molecular weight cutoff membrane. The Pmg solution temperature is ramped down to 4° C. and a Pmg stabilizer, EACA, is added to a final concentration of 20 mM to protect Pmg against damage during pH adjustment from 3.4 to 7.5. Without the addition of EACA, a 67 kDa species appears following the pH swing. The presence of EACA during pH adjustment results in decreased Pmg degradation as compared to pH adjustment without EACA (FIG. 6). Once the pH is adjusted to 7.5, the Pmg solution is diluted 1:1 with 20% glycerol, 4° C., to achieve a final condition of 1 mg Pmg/ml 0.05 M glycine, 0.015 M L-lysine, 0.01 M EACA, 10% glycerol pH 7.5. These conditions have been optimized for minimizing Pm autodegradation. SK is added to this solution at a 100:1 Pmg:SK molar ratio. The SK reaction mixture is mixed at 4° C. for 16 hours to allow activation of Pmg to Pm. The average relative percent purity, as determined by reduced SDS PAGE, of each of 4 groups of protein species (Pmg, Pm HC, Pm LC and impurities/clipped Pm) from 14 SK activation reactions are listed in Table 5.

TABLE 5

Relative Average % of Pmg, Pm (HC, LC) and Impurities/Clipped Pm by Reduced SDS PAGE Following SK Activation; n = 14.

| Protein | Average % Purity | SD |
|---|---|---|
| Pmg | 20.3 | 5.3 |
| Pm | 68.5 | 4.4 |
| Pm Heavy Chain | 49.0 | 2.9 |
| Pm Light Chain | 19.4 | 1.5 |
| Impurities/Clipped Pm | 11.3 | 1.8 |

Figure 7:
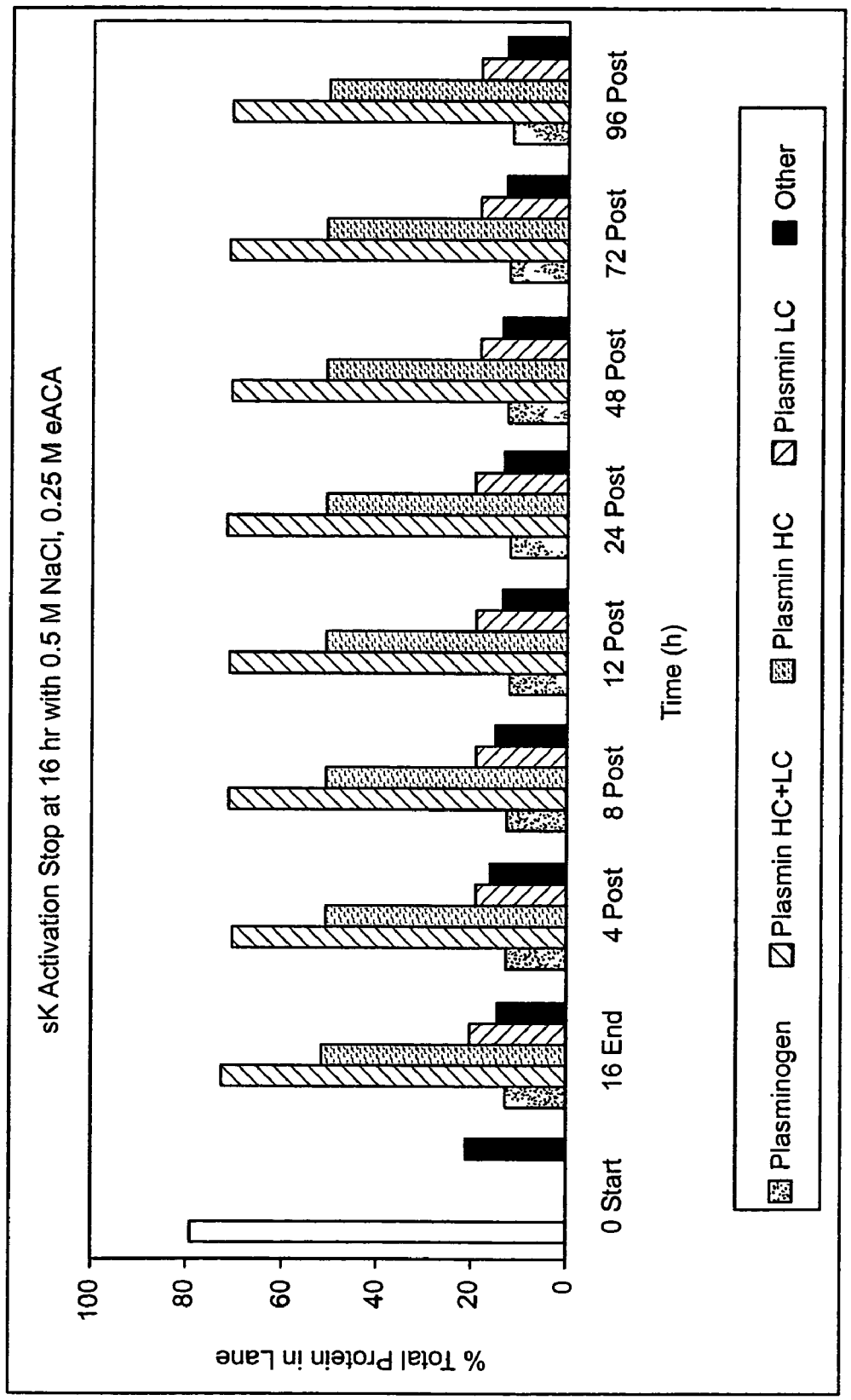
FIG. 7 graphically represents streptokinase activation solution stability following 0.5 M NaCl, 0.25 M $\epsilon$-ACA stop.

The data shows that the SK activation is reproducible and results in only about 11% clipped Pm/impurities while activation of Pmg to Pm is about 80%. To stop the activation and Pm autodegradation reactions, NaCl and EACA are added to final concentrations of 0.5 M and 0.25 M, respectively. This solution is stable with respect to Pm integrity, for at least 4 days at 4° C. FIG. 7 illustrates that there is no change in the Pm purity or Pm autodegradation (Other) over this time period.

Example 5

Figure 8:
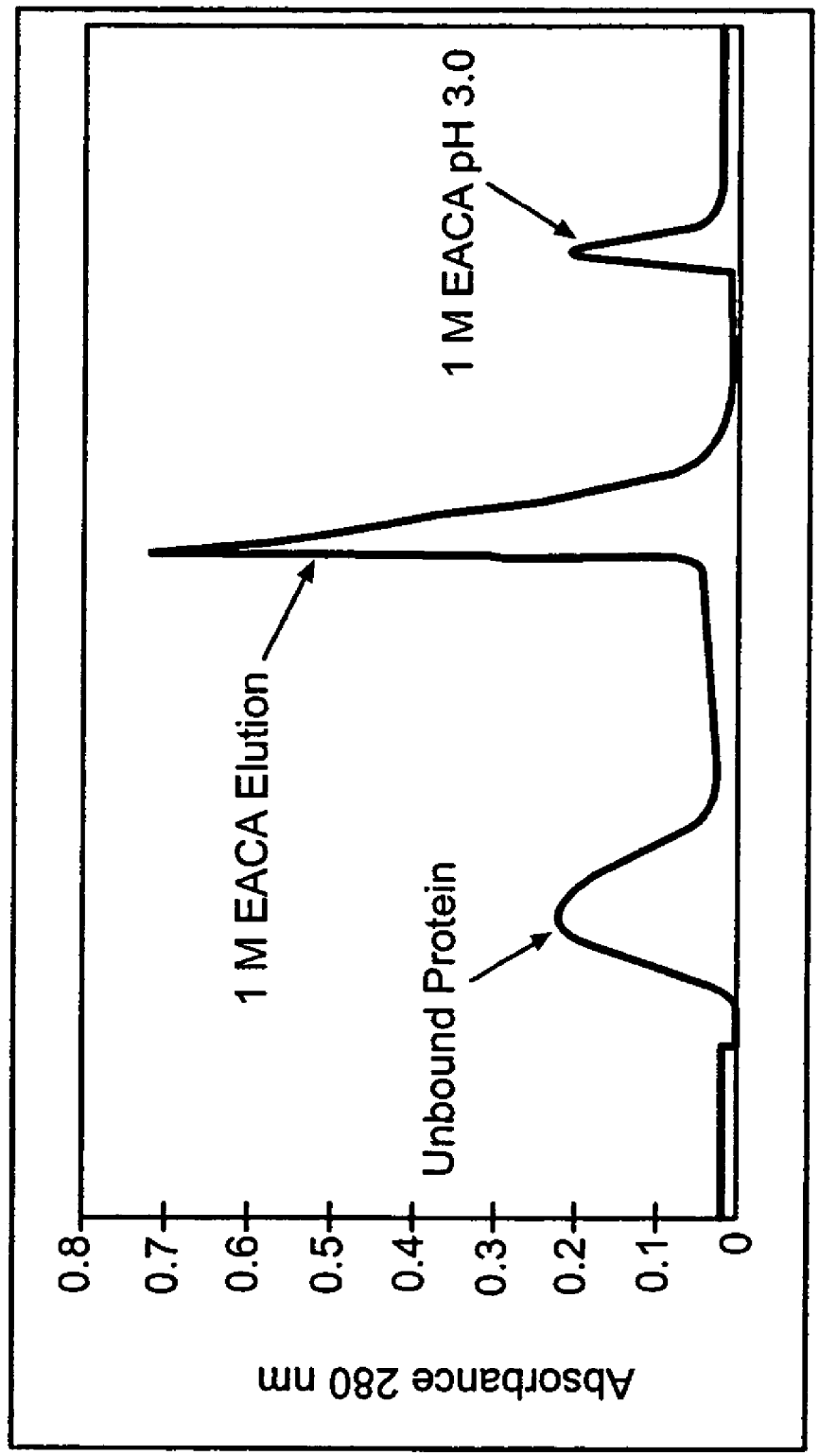
FIG. 8 graphically represents benzamidine SEPHAROSE 6B chromatogram for the affinity purification of SK activated Plasmin (Pm)

Purification of Pm by Benzamidine Affinity Chromatography:

The purpose of benzamidine affinity purification is the separation of unactivated Pmg and impurities, including Pm degradation products, from active Pm. The stable SK activation solution, pH adjusted to 8.5 in 0.05 M glycine, 0.015 M L-lysine, 0.25 M EACA, 0.5 M NaCl, 10% glycerol, is applied to a Benzamidine-SEPHAROSE 6B (Amersham Pharmacia #17-0568-01) column equilibrated with 50 mM Tris, 500 mM NaCl, pH 8.5. The Pm, both clipped and intact, is captured by the affinity resin while the aforementioned impurities flow through the column. The column is washed with the equilibration buffer until the absorbance at 280 nm reaches baseline. The bound Pm is then eluted in either one of two ways: 1) removing the resin and eluting in batch format with 0.1 M Glycine, 0.03 M Lysine pH 3.4; 2) eluting in a column format with 1 M EACA pH 7.5. Elution with EACA pH 7.5 removes only the intact Pm while damaged Pm remains bound to the resin. FIG. 8 shows a typical column format EACA elution profile, including a low pH EACA step to strip all remaining protein. Elution buffer excipient concentration (0.25 to 1.0 M EACA), salt concentration (0.1 to 1.0 M NaCL), and pH (5.0-7.5) conditions can be adjusted to accomplish the goal of purifying intact Pm.

The batch elution profile consists only of the unbound protein peak as the resin is then removed from the column for Pm elution. The Pm captured and eluted from the affinity resin is 87-91% intact (non-autodegraded) as illustrated in FIG. 9 and ≧99% total Pm. The elution of Pm from the benzamidine resin with EACA was unexpected as lysine derivatives such as EACA interact with the heavy chain of Pm while benzamidine interacts with the light chain.

Example 6

Removal of the Pmg Activator SK

The purpose of these steps is to remove the Pmg activator SK such that the only remaining fibrin clot dissolution activity is that of Pm. The benzamidine affinity step removes >99% of the SK from the Pm as is illustrated in Table 6.

TABLE 6

SK removal, as determined by ELISA, by benzamidine affinity chromatography and hydrophobic interaction chromatography.

| Plasmin Process Step | Streptokinase (ng/ml) |
|---|---|
| SK activation | 1930.1 |
| Benzamidine-SEPHAROSE unbound | 1549.5 |
| Benzamidine-SEPHAROSE eluted Pm | 1.9 |
| HIC Unbound Pm | 0.7 |
| HIC NaOH strip (SK) | 1.3 |
| Final Formulation Pm | <0.5 |

Figure 10:
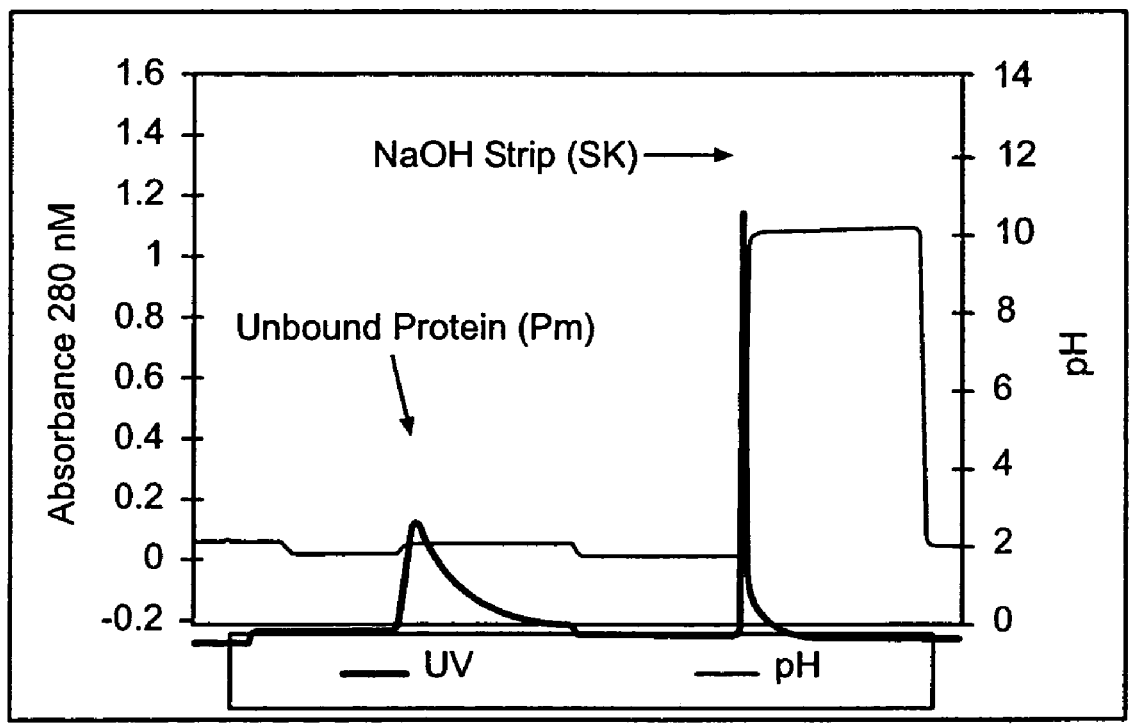
FIG. 10 graphically depicts the hydrophobic interaction chromatography (Octyl-SEPHAROSE 4 FF) chromatogram for the removal of streptokinase.
Figure 11:
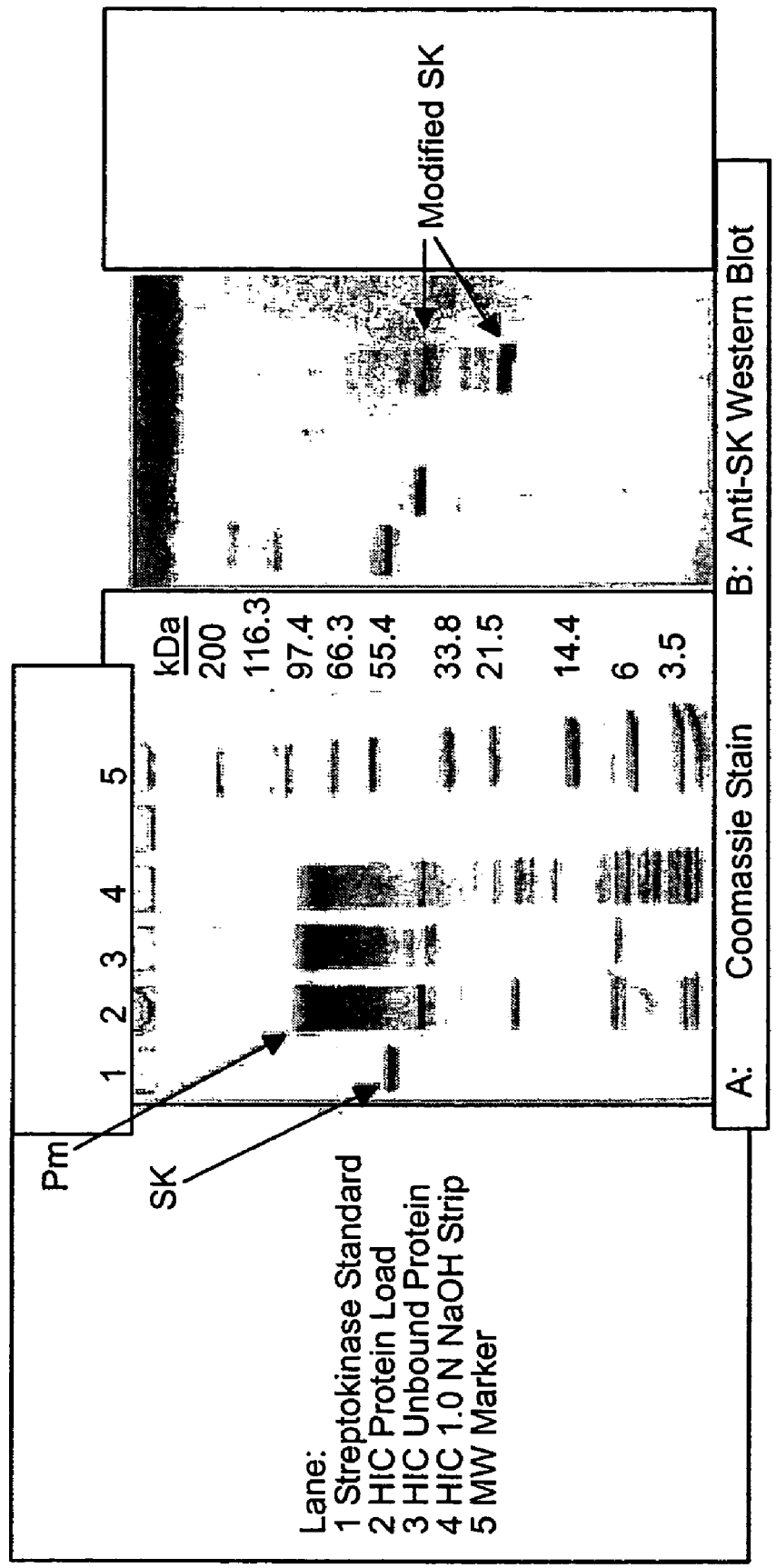
FIG. 11 depicts a non-reduced SDS PAGE and anti-SK Western Blot.

The hydrophobic interaction step using Octyl SEPHAROSE 4 FF (Amersham Pharmacia #17-0946-02) acts as a polishing step to remove essentially any remaining SK. The final sterile Pm product has no detectable SK by ELISA. The 1 M EACA eluate pH 7.5, from the benzamidine affinity column, is adjusted to pH 3.4 and $(NH_4)_2SO_4$ is added to a final concentration of 0.1 M. This acts as the protein load for the Octyl-SEPHAROSE 4 FF column. The column is equilibrated with 0.1 M $(NH_4)_2SO_4$, 0.1 M Glycine, 30 mM Lysine pH 3.4. Pm flows through the column while SK binds to the column and is separated from Pm. The captured SK is removed from the resin along with 0.1 to 1.0 N NaOH. FIG. 10 is an Octyl-SEPHAROSE 4 FF chromatogram from a proof of principle experiment. Pmg and SK were mixed at a 2:1 Pmg:SK molar ratio and subjected to Octyl-SEPHAROSE 4 FF chromatography. The high levels of SK were used so it could be tracked throughout the chromatographic cycle using an anti-SK western blot. FIG. 11 illustrates the removal of SK from the Pm by SDS PAGE and anti-SK western blot. The SK standard (panels A and B; lane 1) migrates true to its molecular weight of 47 kDa. Once mixed with Pmg, the SK is modified and migrates faster and as several species. There is no detectable SK in the unbound protein fraction, which contains the bulk of the Pm, by anti-SK western blot (panel B; lane 3).

Results for final sterile preparations of Pm purified by benzamidine affinity and HIC chromatographies, as described above, are listed in Table 7.

TABLE 7

Relative Average % Purity of Pm (HC, LC) by Reduced SDS PAGE Following HIC; n = 2.

| Protein | Average % Purity |
|---|---|
| Pmg | 0.0 |
| Pm | 95.5 |
| Pm Heavy Chain | 66.5 |
| Pm Light Chain | 29.0 |
| Impurities/Clipped Pm | 4.5 |

Examples 7 through 15 below show additional embodiments of the process of the invention for preparation of plasmin from the Caprylate Cake I starting material.

Example 7

Caprylate Cake I (CCI) Extraction of Plasminogen

Caprylate Cake I (CCI) is suspended in 10 volumes (w/w) of pH 8.0, 0.05 M phosphate buffer containing 0.2 M lysine, 0.25% (w/w) CAB-O-SIL M-5P fumed silica (Cabot Corp. Tuscola, Ill.), and 3.5% (w/w) PEG 3350. These components are mixed at ambient temperature until the CCI becomes a homogeneous suspension by visual examination (not less than 4 hours). During this time, the pH is checked hourly, and if the pH drops below 7.30, 1.0 N NaOH is added to adjust the pH to 7.30-7.60 (target pH 7.50) (the pH drops during extraction due to the low pH (5.0) of the CCI).

After suspension is complete, 1% (w/w) of CELPURE P1000 filter aid (Sigma-Aldrich Co., St. Louis, Mo.) is added and mixed until evenly dispersed. The suspension is then filtered using CUNO 90 SP filter pads (Cuno, Inc., Meriden, Conn.) using press filtration (target 20 psi). Prior to filtration, the press and filters are rinsed with cold water for injection (CWFI). The filter is rinsed with 1.5 cake volumes (w/w) of rinse buffer pH 7.3, 0.05 M phosphate buffer containing 0.2 M lysine, and 3.5% (w/w) PEG 3350.

The press filtrate is cooled to between 10° C. and 14° C. (target 12° C.) and 3 M NaCl is added to a final concentration of 0.5 M. The solution is then concentrated to a target of 58% of starting volume by ultrafiltration using a 30 kD polyethersulfone (BIOMAX) PELLICON 2 membrane cassette (Millipore Corporation, Billerica, Mass.). Prior to use, the ultrafiltration system is flushed with WFI until the permeate is between pH 5.0 and 7.0, followed by pre-conditioning with 0.01 M sodium phosphate, 0.5 M NaCl, pH 7.5. During filtration, the temperature is maintained between 10° C. and 14° C.

The concentrated solution is then subjected to diafiltration with not less than 5 volumes of 0.01 M sodium phosphate, 0.5 NaCl, pH 7.5. The solution is maintained between 10° C. and 14° C. When diafiltration is complete, the retentate valve is opened, the permeate valve is closed, and the membrane is swept at maximum retentate flow for 15 to 20 minutes. Using process air, the remaining product is blown out from the ultrafiltration skid/cassettes into the filtrate tank for no more than 2 minutes at 9 to 11 psi.

The diafiltrate is then subjected to ECH lysine-SEPHAROSE 4FF (Amersham Biosciences Corp., Piscataway, N.J.) affinity chromatography for the purification of plasminogen. The pre-equilibration buffer is 0.05 M sodium phosphate, pH 7.5; the equilibration buffer is 0.01 M sodium phosphate, 0.5 NaCl, pH 7.5; and the elution buffer is 0.1 M glycine, 0.03 M L-lysine (HCl), pH 3.0. The entire chromatographic system (buffers, column, bioprocess skid) are allowed to equilibrate to a temperature between 2° C. to 8° C. A MILLIPORE POLYGUARD 0.3 µm filter is placed in-line for running buffers. The diafiltrate is filtered with an OPTI-CAP 0.2 µm nominal filter (Millipore Corp.) or its equivalent prior to chromatography.

The column is pre-equilibrated with 4 column volumes of pre-equilibration buffer. The column is then equilibrated with equilibration buffer until the effluent pH is stabilized at 7.4 to 7.6 and the conductivity is stable at 38 to 48 mS. The diafiltrate is then loaded onto the column while the temperature is maintained at between 2° C. and 8° C. The column is washed with 4 volumes of equilibration buffer. The column is eluted with lysine elution buffer and plasminogen is collected when the pH slope is −0.5. Collection is terminated when the UV absorbancy of the eluate peak is no more than 0.1 AU (absorbance units). All buffers, diafiltrate load, and washes are run in the downward direction at a flow rate of 100 cm/hr.

An alternative to ultrafiltration/diafiltration (UF/DF) for removal of lysine is cation-exchange (CIEX) column chromatography. Using a resin with a high ionic capacity and low pore retention (e.g., Dowex 50Wx8 100-200 mesh; Dow Chemcals) it is possible to bind only small molecules like lysine, while proteins remain unbound in the flowthrough fraction. The CIEX, and then the lysine column are equilibrated with 0.05 M sodium phosphate, pH 7.0 to 7.5, and operated throughout at chilled or ambient temperature (2° C. to 22° C.). The CUNO filtrate is filtered with an OPTICAP 0.2 µm nominal filter (Millipore Corp.) or its equivalent prior to chromatography, then applied onto the CIEX column at 50 cm/h. The unbound protein in the CIEX column flowthrough are then applied directly to the lysine affinity column, connected in series, to purify the plasminogen. The lysine column is eluted with lysine elution buffer and plasminogen is collected when the pH slope is −0.5. Collection is terminated when the UV absorbancy of the eluate peak is no more than 0.1 AU (absorbance units). All buffers, CUNO filtrate load, and washes are run in the downward direction at a flow rate of 100 cm/hr.

The eluate is frozen at no more than −20° C. for storage.

Example 8

Activation of Plasminogen

Plasminogen prepared according to Example 7 is activated to plasmin with streptokinase as follows:

Frozen lysine eluate (plasminogen) is thawed to a target temperature of 22° C. (20° C. to 24° C.). Plasminogen is incubated with sodium caprylate for viral inactivation for no longer than 1 hour, at a final sodium caprylate concentration of 0.0042 M (0.0034 to 0.0048 M) at a target pH of 3.4 (3.1 to 3.5), with the temperature maintained at the target of 22° C.

Following caprylate incubation, the plasminogen solution is diluted to 1.70 $A_{280}$ (1.45-1.95 range) using an Activation Dilution Buffer of 0.1 M glycine, 0.03 M L-lysine, target pH of 3.40 (3.15 to 3.45). Plasminogen is activated to plasmin with streptokinase at a molar ratio of 100:1, plasminogen to streptokinase, in 0.010 M EACA, 0.010 M sodium phosphate, pH 7.0 (6.90 to 7.10), at a target temperature of 5° C. (2° C. to 8° C.), for 8 hours (7.5 to 8.5). The activation is quenched by addition of EACA and NaCl to a final concentration of 0.25 M EACA and 0.5 M NaCl. The pH is adjusted to a target of 8.50 (8.40 to 8.60) with 1.0 N sodium hydroxide.

Activated plasmin is purified using benzamidine-SEPHAROSE 4FF (Low Sub) affinity resin (Amersham Biosciences Corp., Piscataway, N.J.). The benzamidine-SEPHAROSE resin is poured into a 450×500 column. The equilibration (wash) buffer is 0.05 M Tris-base, 0.5 M NaCl, with a target pH of 8.50 (8.40-8.60). Elution buffer is 0.25 M EACA, 0.15 M NaCl, with a target pH of 6.00 (5.90-6.10). All buffers and plasmin flow in the downward direction on the column at a flow rate of 100 cm//hr unless noted specifically as otherwise. The column is equilibrated with wash buffer until effluent pH is stable at 8.25 to 8.75 and until conductivity is stable at 36 to 48 mS. Activated plasmin is then loaded onto the column while maintaining the temperature between 2° C. and 8° C. The column is washed with no less than 3 column volumes of wash buffer and the plasmin is eluted with elution buffer. The eluate is adjusted to a target pH of 3.40 (3.30-3.50) with 1.0 N HCl with mixing at 2° C. to 8° C.

Example 9

Removal of Streptokinase

The benzamidine-SEPHAROSE eluate is further processed for removal of streptokinase by octyl-SEPHAROSE 4FF hydrophobic interaction chromatography (resin available from Amersham Biosciences Corp., Piscataway, N.J.). The resin is poured into a 140×500 column, packed, and qualified according to the resin manufacturer's instructions. The octyl-SEPHAROSE equilibration (wash) buffer is 0.1 M glycine, 0.03 M L-lysine, 0.1 M ammonium sulfate, at a target pH of 3.40 (3.30-3.50). A MILLIPORE POLYGUARD 0.3 µm filter is placed in-line when running buffers and loading sample. Buffers, column, and bioprocess skid are all equilibrated to between 2° C. and 8° C. prior to use.

All buffers and sample load are run in a downward direction at a flow rate of 200 cm/hr unless otherwise specifically noted. The packed column is equilibrated with wash buffer until the effluent pH is stable at 3.00 to 3.50 and the conductivity is stable at 16 mS to 26 mS. After ammonium sulfate is added to the purified plasmin solution (benzamidine-SEPHAROSE eluate prepared as in Example 8) to 0.1 M, the plasmin is applied to the resin at a target pH of 3.40 (3.30-3.50), and at a temperature between 2° C. and 8° C. The plasmin is collected in the flow-through.

Example 10

Nanofiltration of Plasmin

The plasmin solution (the octyl-SEPHAROSE flow-through) from Example 9 is subjected to nanofiltration using PLANOVA 15N filters (ASAHI NF 1.0 m² membrane, 15N) (Asahi Kasei America, Inc., Buffalo Grove, Ill.). Prior to nanofiltration, the octyl-SEPHAROSE flow-through is subjected to filtration using a MILLIPORE 0.1 micron 4" or 10" OPTICAP filter capsule. A peristaltic pump and silicon tubing are used for these filtration processes. A leakage test is performed on the nanofilter prior to use.

The capacity of the nanofilter is no more than 30 g plasmin/m². An in-line pressure gauge is used for feed during nanofiltration. The system is rinsed with octyl-SEPHAROSE wash buffer (see Example 9), and the plasmin-containing flow-through is pumped through the nanofilter at a target pressure of 12 psi (10 psi -14 psi).

Example 11

Ultrafiltration/Diafiltration of Plasmin Nanofiltrate

A peristaltic pump with BIOPRENE tubing (Watson-Marlow Bredel Inc, Wilmington, Mass.) is used in conjunction with a PELLICON-2 steel holder and MILLIPORE 10 kD BIOMAX UF cassettes (Millipore Corporation, Billerica, Mass.). The process temperature is maintained between 2° C. and 12° C. The ultrafiltration system is flushed with CWFI until the permeate pH is between 5.00 and 7.00. The system is then flushed with 0.002 M acetic acid until the permeate and retentate pHs are between 3.10 and 3.50. The system is cooled to between 2.0° C. and 8.0° C. before product is committed to the system. The nanofiltrate of Example 10 is then concentrated to a target $A_{280}$ of 5.1 (4.0 to 6.0) by ultrafiltration.

The concentrated solution is then diafiltered with no less than 5 volumes of 0.002 M acetic acid, target pH of 3.20 (3.10-3.30) while the temperature is maintained between 2° C. and 12° C. The diafiltered solution is concentrated to a target $A_{280}$ of 12.0 (11.0-13.0), and the pH is adjusted if necessary to between 3.10 and 3.30 (target 3.20).

Example 12

Plasmin Formulation

The diafiltered plasmin from Example 11 is formulated at 5 mg plasmin per ml of a solution containing 5.1% trehalose-dihydrate, 2 mM acetic acid, pH 3.1-3.3 (target 3.2). The plasmin can be bulked with trehalose and then adjusted to a target potency of 5.25 mg/ml and transferred into STEDIM 4 liter EVA bags (STEDIM, Inc., Concord, Calif.).

The plasmin can be optionally frozen at no more than −50° C. and stored at no more than −20° C.

Example 13

Effect of CAB-O-SIL M-5P on Plasminogen and Lipid Levels in PEG/CUNO Filtrate

Experiments (with 3.0% PEG) showed that the addition of CAB-O-SIL M-5P to Caprylate Cake I (CCI) suspensions greatly reduced lipid levels with no loss in plasminogen recovery. To determine an appropriate CAB-O-SIL M-5P concentration to further reduce filtrate lipid levels, CCI suspension was treated for three hours with 3.0% PEG and 0.1%, 0.25%, 0.5% or no CAB-O-SIL M-5P, followed by depth filtration through CUNO 90SP pads. The PEG/CUNO filtrates were analyzed for plasminogen (by potency) and lipid concentrations and the results are shown below.

TABLE 8

Effect of CAB-O-SIL on Plasminogen and Lipid Levels

| CAB-O-SIL M-5P (%) | Plasminogen (g/L) | Cholesterol (g/ml) | Triglycerides (g/ml) |
|---|---|---|---|
| 0.00 (control) | 0.104 | 46 | <40 |
| 0.10 | 0.100 | 20 | <40 |
| 0.25 | 0.102 | <20 | <40 |
| 0.50 | 0.097 | <20 | <40 |

Increasing concentrations of CAB-O-SIL M-5P resulted in increased lipid clearance without impact on plasminogen recovery. Based on these findings, a concentration of 0.25% CAB-O-SIL M-5P was selected as the lowest concentration providing lipid removal to the level of assay detection.

Example 14

Effect of CAB-O-SIL M-5P on Pathogenic Prion Protein Clearance

Figure 12:
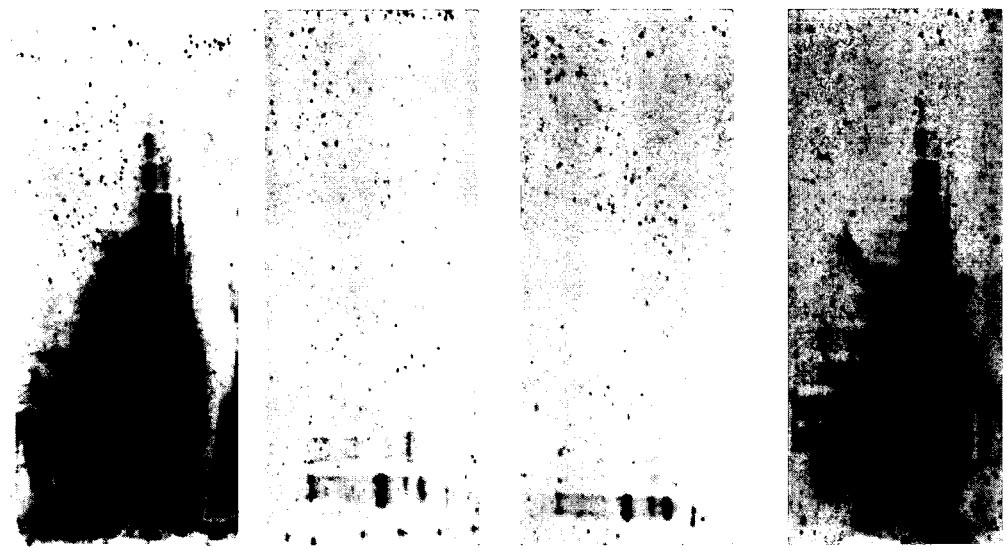
FIG. 12 depicts Western blots illustrating the clearance of prion proteins by including fumed silica during purification of plasminogen.

Caprylate Cake I (CCI) was suspended in 10 volumes Tris buffer (pH 7). After 2 hours of mixing, 1% CELPURE P1000 filter aid was added and mixed for 2 minutes. Crude sheep brain homogenate (SBH) was added, and an input sample was removed. The remaining sample was divided into two 100 ml aliquots. One aliquot received 0.25% CAB-O-SIL, the other no CAB-O-SIL. The results are shown in FIG. 12. A "prove" sample (containing the same SBH innoculate, but subjected to no processing prior to parallel analysis for prion protein) showed 5 logs of $PrP^{Sc}$. The "No Cab-O-Sil" filtrate had 3 logs of $PrP^{Sc}$. The signals present in the filtrate of the "0.25% Cab-O-Sil" were not PrP-related and the use of 0.25% CAB-O-SIL improved the clearance to 3 logs over the "No Cab-O-Sil" treated sample.

Example 15

Use of Aluminum Hydroxide for Pathogenic Prion Protein Clearance

Bovine serum albumin (BSA) was dissolved in phosphate buffered saline (PBS) to create a solution at 1 mg/ml BSA. The BSA solution was "spiked" with scrapie brain homogenate (SBH; prepared using hamster brains infected with the 263K hamster-adapted agent), highly clarified prior to use by centrifugation at 10,000 g for 10 minutes to a final concentration of approximately 1%. CAB-O-SIL M-5P silica (CAB-O-SIL) was added at various concentrations, followed by vortexing and filtration using a 0.8 μm filter (filtration alone was estimated to account for approximately 0.5 log reduction in $PrP^{Sc}$). These samples were used to evaluate aluminum hydroxide ($Al_2O_3$, 1.9-2.2% (w/v) as a gel or slurry—represent also as $Al(OH)_3$ or aluminum hydroxide herein) (ALHYDROGEL, Superfos Biosector A/S, Denmark) as an agent useful for prion clearance. The volume/volume percentages below and through refer to the proportion of the ALHYROGEL product added Various amounts of $Al(OH)_3$ (final concentrations of 0 to 18% (v/v) as indicated in Table 1) were added to samples containing SBH, and the samples were mixed. The samples were then centrifuged at 5100 g for 5 minutes, and the supernatant and pellet were assayed for $PrP^{Sc}$. For the 1% SBH, clearance was greater than 4 logs for aluminum hydroxide when treated with more than 4.5% (v/v). For 0.1% SBH clearance was greater than 3 logs for aluminum hydroxide greater than 1% (v/v).

In order to validate a model system for evaluating $PrP^{Sc}$ clearance according to a particular embodiment of the present invention, a scaled-down model for Caprylate Cake I (CCI) extraction (as discussed above regarding plasminogen purification procedure) was characterized with respect to the clearance effect of the PEG Precipitation/Depth Filtration Steps. The purpose of this study was to establish a bench-scale model of the CCI Extraction and PEG Precipitation/Depth Filtration step in the Plasminogen Process under standard conditions. Once established, the model system was used to evaluate $PrP^{Sc}$ clearance across the process step.

Briefly, CCI was resuspended in 0.1 M TRIZMA base extraction buffer (pH 10.5) at 40° C. while mixing for 2-3 hours. Following extraction, the pH of the solution was adjusted to 7.5 and temperature of the extract increased to 20° C. L-lysine was added to the extract to a final concentration of 100 mM, while maintaining a pH of 7.5. Polyethylene glycol (PEG) was added to a final concentration of 3% (w/w) followed by the addition of HYFLO SUPERCEL filter aid (Celite Corporation, Lompoc, Calif.) to a final concentration of 4% (w/w). The extract was then filtered through a CUNO SP-30 filter pad and filtrate collected. Samples were collected from initial CCI extract, filtrate, and extract. Total protein determined by $A_{280}$ and plasminogen recovery determined by immunonephelometry. Recovery analysis indicated very little protein loss across this step.

Next, $PrP^{Sc}$ clearance during the CCI and PEG precipitation/depth filtration step was evaluated. The purpose of this experiment was to determine the amount of $PrP^{Sc}$ removed during the extraction of the CCI and PEG precipitation/depth filtration steps. The protocol was the same as described above, except that during the extraction of CCI, 1 ml of 10% crude SBH was added into 100 ml of the extract resulting in 0.1% final SBH concentration. The paste retained by the CUNO SP-30 filter was resuspended to original volume in TBS. Samples from the Prove (spiked extract prior to filtration), filtrate, and from the paste resuspension were analyzed for both plasminogen and $PrP^{Sc}$ by Western analysis. The steps above, with no aluminum hydroxide or CAB-O-SIL, resulted in 1 log of clearance $PrP^{Sc}$.

The effect of 10% (v/v) $Al(OH)_3$ (ALHYDROGEL, Superfos Biosector A/S, Denmark) on plasminogen recovery and $PrP^{Sc}$ clearance during the PEG precipitation/depth filtration was determined. Protocol was as described above in Example 4, except that, following the addition of 3% PEG, 10% $Al(OH)_3$ (v/v) was added. The paste retained by the CUNO SP-30 filter was resuspended to original volume in TBS. Samples from the Prove (spiked extract prior to filtration), filtrate, and from the paste resuspension were analyzed for both plasminogen and $PrP^{Sc}$ by Western analysis. Including $Al(OH)_3$ (v/v), as indicated above, resulted in an increase in $PrP^{Sc}$ clearance by 2 logs (approximately 3 logs with versus 1 log without).

The effect of 3% $Al(OH)_3$ on $PrP^{Sc}$ clearance during processing of Caprylate Cake I (CCI) was also determined. CCI was extracted and processed as described above. In one experiment, both SBH spike and 3% $Al(OH)_3$ (v/v) were added prior to the cloth (porous polypropylene filtration. Samples were removed from the Input (Prove) and cloth filtrate. The presence of $PrP^{Sc}$ was determined in each sample by Western analysis. Inclusion of 3% $Al(OH)_3$ (v/v) resulted in 2 logs of clearance of $PrP^{Sc}$. Without Al(OH)3, clearance was 0 logs.

While specific embodiments have been set forth as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

What is claimed is:

1. A method for preparing a plasmin solution comprising:
- cleaving a plasminogen in the presence of a plasminogen activator to yield an active plasmin;
- substantially removing the plasminogen activator from the active plasmin by binding the active plasmin to an active plasmin-specific absorbent material to form a bound plasmin wherein the active plasmin-specific absorbent material comprises benzamidine, and eluting the bound plasmin with an excipient solution having a pH from about 2.5 to about 9.0 to form a plasmin solution; and
- buffering the plasmin solution with a low pH, low buffering capacity agent to form a reversibly inactive acidified plasmin solution having a pH of approximately 1 to 4.

2. The method of claim 1, wherein the excipient solution has a pH from about 4.0 to about 7.5.

3. The method of claim 1, wherein the excipient solution has a pH of about 6.0.

4. The method of claim 1, wherein the plasminogen activator is further removed by hydrophobic interaction.

5. The method of claim 1, further comprising nanofiltration of the plasmin solution.

6. The method of claim 5, wherein the nanofiltration is carried out using a filter membrane characterized by an average pore size of approximately 15 nm.

7. The method of claim 1, wherein the plasminogen is cleaved in the presence of at least one excipient that is an omega-amino acid.

8. The method of claim 1, wherein the plasminogen is cleaved in the presence of at least one omega-amino acid selected from the group consisting of lysine, epsilon amino caproic acid, tranexamic acid, poly lysine, arginine, and combinations thereof.

9. The method of claim 1, wherein the plasmin is eluted in a solution comprising at least one salt, the solution having a conductivity from about 5 mS to about 100 mS.

10. The method of claim 9, wherein the at least one salt is sodium chloride.

11. The method of claim 10, wherein the sodium chloride is present at a concentration of from about 50 mM to about 1000 mM.

12. The method of claim 10, wherein the sodium chloride is present at a concentration of about 150 mM.

13. The method of claim 1, wherein the plasminogen is cleaved using a catalytic concentration of a plasminogen activator that is selected from the group consisting of immobilized plasminogen activators, soluble plasminogen activators, and combinations thereof.

14. The method of claim 1, wherein the plasminogen activator is selected from the group consisting of streptokinase, urokinase, tissue plasminogen activator and combinations thereof.

15. The method of claim 1, wherein the plasminogen activator is soluble streptokinase.

16. The method of claim 1, wherein the plasminogen activator is immobilized on a solid support medium comprising a beaded form of agarose gel.

17. The method of claim 1, wherein the low pH, low buffering capacity agent comprises a component selected from the group consisting of an amino acid, a derivative of at least one amino acid, an oligopeptide which includes at least one amino acid, and combinations thereof.

18. The method of claim 1, wherein the low pH, low buffering capacity agent comprises a component selected from the group consisting of acetic acid, citric acid, hydrochloric acid, carboxylic acid, lactic acid, malic acid, tartaric acid, benzoic acid, seine, threonine, methionine, glutamine, alanine, glycine, isoleucine, valine, aspartic acid, and combinations thereof.

19. The method of claim 1, wherein the low buffering capacity agent is present in the reversibly inactive acidified plasmin at a concentration at which the pH of the acidified plasmin is raised to neutral pH by adding serum in an amount no more than about 5 times the volume of the acidified plasmin.

20. The method of claim 1, wherein the reversibly inactive acidified plasmin solution has a pH between about 2.5 to about 4.

21. The method of claim 1, further including stabilizing the reversibly inactive acidified plasmin by adding a stabilizing agent selected from the group consisting of a polyhydric alcohol, pharmaceutically acceptable carbohydrates, salts, glucosamine, thiamine, niacinamide, and combinations thereof.

22. The method of claim 21, wherein the salts are selected from the group consisting of sodium chloride, potassium chloride, magnesium chloride, calcium chloride and combinations thereof.

23. The method of claim 1, further including stabilizing the reversibly inactive acidified plasmin by adding a sugar or sugar alcohol selected from the group consisting of glucose, maltose, mannitol, sorbitol, sucrose, lactose, trehalose, and combinations thereof.

* * * * *

(12) EX PARTE REEXAMINATION CERTIFICATE (9672nd)
United States Patent
Bradley et al.

(10) Number: US 7,544,500 C1
(45) Certificate Issued: May 21, 2013

(54) PROCESS FOR THE PRODUCTION OF A REVERSIBLY INACTIVE ACIDIFIED PLASMIN COMPOSITION

(75) Inventors: Rita T. Bradley, Cary, NC (US); Scott A. Cook, Garner, NC (US); Christopher A. Dadd, Holly Springs, NC (US); Jonathan D. Kent, Holly Springs, NC (US); Marina N. Korneyeva, Raleigh, NC (US); Valery V. Novokhatny, Raleigh, NC (US); James F. Rebbeor, Garner, NC (US); Christopher J. Stenland, Cary, NC (US); Jonathan S. Strauss, Walnut Creek, NC (US); Jarrett C. Terry, Raleigh, NC (US); Jeffrey A. Yuziuk, Garner, NC (US)

(73) Assignee: Morgan Stanley Senior Funding, Inc., New York, NY (US)

Reexamination Request:
No. 90/010,765, Jan. 11, 2010

Reexamination Certificate for:
Patent No.: 7,544,500
Issued: Jun. 9, 2009
Appl. No.: 10/692,105
Filed: Oct. 23, 2003

Related U.S. Application Data

(63) Continuation-in-part of application No. 10/143,156, filed on May 10, 2002, now abandoned, which is a continuation of application No. PCT/US00/42143, filed on Nov. 13, 2000, which is a continuation-in-part of application No. 09/438,331, filed on Nov. 13, 1999, now Pat. No. 6,355,243.

(51) Int. Cl.
*C12N 9/50* (2006.01)
*A61K 38/00* (2006.01)
*A61K 38/48* (2006.01)
*A61K 47/02* (2006.01)
*A61K 47/12* (2006.01)
*A61K 47/18* (2006.01)
*A61K 47/26* (2006.01)
*C12N 9/68* (2006.01)
*C12N 9/70* (2006.01)

(52) U.S. Cl.
USPC .................. 435/219; 435/216; 435/217

(58) Field of Classification Search
None
See application file for complete search history.

(56) References Cited

To view the complete listing of prior art documents cited during the proceeding for Reexamination Control Number 90/010,765, please refer to the USPTO's public Patent Application Information Retrieval (PAIR) system under the Display References tab.

*Primary Examiner* — Bruce Campell

(57) ABSTRACT

Disclosed is both a process for producing a reversibly inactive acidified plasmin by activating plasminogen and a process for producing a purified plasminogen. The produced plasmin is isolated and stored with a low pH-buffering capacity agent to provide a substantially stable formulation. The purified plasminogen is typically purified from a fraction obtained in the separation of immunoglobulin from Fraction II+III chromatographic process and eluted at a low pH. The reversibly inactive acidified plasmin may be used in the administration of a thrombolytic therapy.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-23 are cancelled.

\* \* \* \* \*